(12) United States Patent
Lorkovic

(10) Patent No.: US 7,964,764 B2
(45) Date of Patent: *Jun. 21, 2011

(54) HYDROCARBON SYNTHESIS

(75) Inventor: Ivan M. Lorkovic, Santa Barbara, CA (US)

(73) Assignee: GRT, Inc., Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/683,607

(22) Filed: Jan. 7, 2010

(65) Prior Publication Data

US 2010/0105972 A1 Apr. 29, 2010

Related U.S. Application Data

(63) Continuation of application No. 12/080,594, filed on Apr. 3, 2008, now abandoned, which is a continuation of application No. 11/091,130, filed on Mar. 28, 2005, now abandoned, which is a continuation-in-part of application No. 10/893,418, filed on Jul. 15, 2004, now abandoned.

(60) Provisional application No. 60/487,364, filed on Jul. 15, 2003.

(51) Int. Cl.
C07C 1/00 (2006.01)

(52) U.S. Cl. ........ 585/359; 585/408; 585/469; 585/642; 585/733; 585/943; 585/935

(58) Field of Classification Search .................. None
See application file for complete search history.

(56) References Cited

U.S. PATENT DOCUMENTS

| | | | |
|---|---|---|---|
| 2,168,260 A | 8/1939 | Heisel et al. |
| 2,246,082 A | 6/1941 | Vaughan et al. |
| 2,488,083 A | 11/1949 | Gorin et al. |
| 2,677,598 A | 5/1954 | Crummett et al. |
| 2,941,014 A | 6/1960 | Rothweiler et al. |
| 3,076,784 A | 2/1963 | Huermann et al. |
| 3,172,915 A | 3/1965 | Borkowski et al. |
| 3,246,043 A | 4/1966 | Rosset et al. |
| 3,273,964 A | 9/1966 | Rosset |
| 3,294,846 A | 12/1966 | Livak et al. |
| 3,310,380 A | 3/1967 | Lester |
| 3,346,340 A | 10/1967 | Louvar et al. |
| 3,353,916 A | 11/1967 | Lester |
| 3,353,919 A | 11/1967 | Stockman |
| 3,496,242 A | 2/1970 | Berkowitz et al. |
| 3,562,321 A | 2/1971 | Borkowski et al. |
| 3,598,876 A | 8/1971 | Bloch |
| 3,657,367 A | 4/1972 | Blake et al. |
| 3,670,037 A | 6/1972 | Dugan |
| 3,673,264 A | 6/1972 | Kuhn |
| 3,679,758 A | 7/1972 | Schneider |
| 3,702,886 A | 11/1972 | Argauer et al. |
| 3,705,196 A | 12/1972 | Turner |
| 3,799,997 A | 3/1974 | Schmerling |
| 3,865,886 A | 2/1975 | Schindler et al. |
| 3,876,715 A | 4/1975 | McNulty et al. |
| 3,879,473 A | 4/1975 | Stapp |
| 3,879,480 A | 4/1975 | Riegel et al. |
| 3,883,651 A | 5/1975 | Woitun et al. |
| 3,886,287 A | 5/1975 | Kobayashi et al. |
| 3,894,103 A | 7/1975 | Chang et al. |
| 3,894,104 A | 7/1975 | Chang et al. |
| 3,894,105 A | 7/1975 | Chang et al. |
| 3,894,107 A | 7/1975 | Butter et al. |
| 3,907,917 A | 9/1975 | Forth |
| 3,919,336 A | 11/1975 | Kurtz |
| 3,920,764 A | 11/1975 | Riegel et al. |
| 3,923,913 A | 12/1975 | Antonini et al. |
| 3,928,483 A | 12/1975 | Chang et al. |
| 3,965,205 A | 6/1976 | Garwood et al. |
| 3,974,062 A | 8/1976 | Owen et al. |
| 3,987,119 A | 10/1976 | Kurtz et al. |
| 3,992,466 A | 11/1976 | Plank et al. |
| 4,006,169 A | 2/1977 | Anderson et al. |
| 4,011,278 A | 3/1977 | Plank et al. |
| 4,025,571 A | 5/1977 | Lago |
| 4,025,572 A | 5/1977 | Lago |
| 4,025,575 A | 5/1977 | Chang et al. |
| 4,025,576 A | 5/1977 | Chang et al. |
| 4,035,285 A | 7/1977 | Owen et al. |
| 4,035,430 A | 7/1977 | Dwyer et al. |
| 4,039,600 A | 8/1977 | Chang |
| 4,044,061 A | 8/1977 | Chang et al. |
| 4,046,825 A | 9/1977 | Owen et al. |
| 4,049,734 A | 9/1977 | Garwood et al. |
| 4,052,471 A | 10/1977 | Pearsall |
| 4,052,472 A | 10/1977 | Givens et al. |
| 4,058,576 A | 11/1977 | Chang et al. |
| 4,060,568 A | 11/1977 | Rodewald |

(Continued)

FOREIGN PATENT DOCUMENTS

BR 0210054 8/2004

(Continued)

OTHER PUBLICATIONS

U.S. Appl. No. 60/487,364, filed Jul. 15, 2003, Lorkovic et al.

(Continued)

Primary Examiner — Tam M Nguyen
(74) Attorney, Agent, or Firm — Baker Botts L.L.P.

(57) ABSTRACT

A method of synthesizing hydrocarbons from smaller hydrocarbons includes the steps of hydrocarbon halogenation, simultaneous oligomerization and hydrogen halide neutralization, and product recovery, with a metal-oxygen cataloreactant used to facilitate carbon-carbon coupling. Treatment with air or oxygen liberates halogen and regenerates the cataloreactant.

27 Claims, No Drawings

U.S. PATENT DOCUMENTS

| | | | |
|---|---|---|---|
| 4,071,753 A | 1/1978 | Fulenwider et al. | |
| 4,072,733 A | 2/1978 | Hargis et al. | |
| 4,087,475 A | 5/1978 | Jordan | |
| 4,088,706 A | 5/1978 | Kaeding | |
| 4,092,368 A | 5/1978 | Smith | |
| 4,110,180 A | 8/1978 | Nidola et al. | |
| 4,117,251 A | 9/1978 | Kaufhold et al. | |
| 4,129,604 A | 12/1978 | Tsao | |
| 4,133,838 A | 1/1979 | Pearson | |
| 4,133,966 A | 1/1979 | Pretzer et al. | |
| 4,138,440 A | 2/1979 | Chang et al. | |
| 4,156,698 A | 5/1979 | Dwyer et al. | |
| 4,169,862 A | 10/1979 | Eden | |
| 4,172,099 A | 10/1979 | Severino | |
| 4,187,255 A | 2/1980 | Dodd | |
| 4,194,990 A | 3/1980 | Pieters et al. | |
| 4,197,420 A | 4/1980 | Ferraris et al. | |
| 4,219,680 A | 8/1980 | Konig et al. | |
| 4,249,031 A | 2/1981 | Drent et al. | |
| 4,270,929 A | 6/1981 | Dang Vu et al. | |
| 4,272,338 A | 6/1981 | Lynch et al. | |
| 4,282,159 A | 8/1981 | Davidson et al. | |
| 4,300,005 A | 11/1981 | Li | |
| 4,300,009 A | 11/1981 | Haag et al. | |
| 4,301,253 A | 11/1981 | Warren | |
| 4,302,619 A | 11/1981 | Gross et al. | |
| 4,307,261 A | 12/1981 | Beard, Jr. et al. | |
| 4,308,403 A | 12/1981 | Knifton | |
| 4,311,865 A | 1/1982 | Chen et al. | |
| 4,317,800 A | 3/1982 | Sloterdijk et al. | |
| 4,317,934 A | 3/1982 | Seemuth | |
| 4,317,943 A | 3/1982 | Knifton | |
| 4,320,241 A | 3/1982 | Frankiewicz | |
| 4,333,852 A | 6/1982 | Warren | |
| 4,347,391 A | 8/1982 | Campbell | |
| 4,350,511 A | 9/1982 | Holmes et al. | |
| 4,371,716 A | 2/1983 | Paxson et al. | |
| 4,373,109 A | 2/1983 | Olah | |
| 4,376,019 A | 3/1983 | Gamlen et al. | |
| 4,380,682 A | 4/1983 | Leitert et al. | |
| 4,384,159 A | 5/1983 | Diesen | |
| 4,389,391 A | 6/1983 | Dunn | |
| 4,410,714 A | 10/1983 | Apanel | |
| 4,412,086 A | 10/1983 | Beard, Jr. et al. | |
| 4,418,236 A | 11/1983 | Cornelius et al. | |
| 4,431,856 A | 2/1984 | Daviduk et al. | |
| 4,433,189 A | 2/1984 | Young | |
| 4,433,192 A | 2/1984 | Olah | |
| 4,439,409 A | 3/1984 | Puppe et al. | |
| 4,440,871 A | 4/1984 | Lok et al. | |
| 4,443,620 A | 4/1984 | Gelbein et al. | |
| 4,462,814 A | 7/1984 | Holmes et al. | |
| 4,465,884 A | 8/1984 | Degnan et al. | |
| 4,465,893 A | 8/1984 | Olah | |
| 4,467,130 A | 8/1984 | Olah | |
| 4,467,133 A | 8/1984 | Chang et al. | |
| 4,489,210 A | 12/1984 | Judat et al. | |
| 4,489,211 A | 12/1984 | Ogura et al. | |
| 4,492,657 A | 1/1985 | Heiss | |
| 4,496,752 A | 1/1985 | Gelbein et al. | |
| 4,497,967 A | 2/1985 | Wan | |
| 4,499,314 A | 2/1985 | Seddon et al. | |
| 4,506,105 A | 3/1985 | Kaufhold | |
| 4,509,955 A | 4/1985 | Hayashi | |
| 4,513,092 A | 4/1985 | Chu et al. | |
| 4,513,164 A | 4/1985 | Olah | |
| 4,523,040 A | 6/1985 | Olah | |
| 4,524,227 A | 6/1985 | Fowles et al. | |
| 4,524,228 A | 6/1985 | Fowles et al. | |
| 4,524,231 A | 6/1985 | Fowles et al. | |
| 4,538,014 A | 8/1985 | Miale et al. | |
| 4,538,015 A | 8/1985 | Miale et al. | |
| 4,540,826 A | 9/1985 | Banasiak et al. | |
| 4,543,434 A | 9/1985 | Chang | |
| 4,544,781 A | 10/1985 | Chao et al. | |
| 4,547,612 A | 10/1985 | Tabak | |
| 4,550,217 A | 10/1985 | Graziani et al. | |
| 4,550,218 A | 10/1985 | Chu | |
| 4,568,660 A | 2/1986 | Klosiewicz | |
| 4,579,977 A | 4/1986 | Drake | |
| 4,579,992 A | 4/1986 | Kaufhold et al. | |
| 4,579,996 A | 4/1986 | Font Freide et al. | |
| 4,587,375 A | 5/1986 | Debras et al. | |
| 4,588,835 A | 5/1986 | Torii et al. | |
| 4,590,310 A | 5/1986 | Townsend et al. | |
| 4,599,474 A | 7/1986 | Devries et al. | |
| 4,605,796 A | 8/1986 | Isogai et al. | |
| 4,605,803 A | 8/1986 | Chang et al. | |
| 4,621,161 A | 11/1986 | Shihabi | |
| 4,621,164 A | 11/1986 | Chang et al. | |
| 4,633,027 A | 12/1986 | Owen et al. | |
| 4,634,800 A | 1/1987 | Withers, Jr. et al. | |
| 4,642,403 A | 2/1987 | Hyde et al. | |
| 4,642,404 A | 2/1987 | Shihabi | |
| 4,652,688 A | 3/1987 | Brophy et al. | |
| 4,654,449 A | 3/1987 | Chang et al. | |
| 4,655,893 A | 4/1987 | Beale | |
| 4,658,073 A | 4/1987 | Tabak | |
| 4,658,077 A | 4/1987 | Kolts et al. | |
| 4,665,259 A | 5/1987 | Brazdil et al. | |
| 4,665,267 A | 5/1987 | Barri | |
| 4,665,270 A | 5/1987 | Brophy et al. | |
| 4,675,410 A | 6/1987 | Feitler et al. | |
| 4,690,903 A | 9/1987 | Chen et al. | |
| 4,695,663 A | 9/1987 | Hall et al. | |
| 4,696,985 A | 9/1987 | Martin | |
| 4,704,488 A | 11/1987 | Devries et al. | |
| 4,704,493 A | 11/1987 | Devries et al. | |
| 4,709,108 A | 11/1987 | Devries et al. | |
| 4,720,600 A | 1/1988 | Beech, Jr. et al. | |
| 4,720,602 A | 1/1988 | Chu | |
| 4,724,275 A | 2/1988 | Hinnenkamp et al. | |
| 4,735,747 A | 4/1988 | Ollivier et al. | |
| 4,737,594 A | 4/1988 | Olah | |
| 4,748,013 A | 5/1988 | Saito et al. | |
| 4,769,504 A | 9/1988 | Noceti et al. | |
| 4,774,216 A | 9/1988 | Kolts et al. | |
| 4,775,462 A | 10/1988 | Imai et al. | |
| 4,777,321 A | 10/1988 | Harandi et al. | |
| 4,781,733 A | 11/1988 | Babcock et al. | |
| 4,783,566 A | 11/1988 | Kocal et al. | |
| 4,788,369 A | 11/1988 | Marsh et al. | |
| 4,788,377 A | 11/1988 | Chang et al. | |
| 4,792,642 A | 12/1988 | Rule et al. | |
| 4,795,732 A | 1/1989 | Barri | |
| 4,795,737 A | 1/1989 | Rule et al. | |
| 4,795,843 A | 1/1989 | Imai et al. | |
| 4,795,848 A | 1/1989 | Teller et al. | |
| 4,804,797 A | 2/1989 | Minet et al. | |
| 4,804,800 A | 2/1989 | Bortinger et al. | |
| 4,808,763 A | 2/1989 | Shum | |
| 4,814,527 A | 3/1989 | Diesen | |
| 4,814,532 A | 3/1989 | Yoshida et al. | |
| 4,814,535 A | 3/1989 | Yurchak | |
| 4,814,536 A | 3/1989 | Yuchak | |
| 4,849,562 A | 7/1989 | Buhs et al. | |
| 4,849,573 A | 7/1989 | Kaefing | |
| 4,851,602 A | 7/1989 | Harandi et al. | |
| 4,851,606 A | 7/1989 | Ragonese et al. | |
| 4,886,925 A | 12/1989 | Harandi | |
| 4,886,932 A | 12/1989 | Leyshon | |
| 4,891,463 A | 1/1990 | Chu | |
| 4,895,995 A | 1/1990 | James, Jr. et al. | |
| 4,899,000 A | 2/1990 | Stauffer | |
| 4,899,001 A | 2/1990 | Kalnes et al. | |
| 4,899,002 A | 2/1990 | Harandi et al. | |
| 4,902,842 A | 2/1990 | Kalnes et al. | |
| 4,925,995 A | 5/1990 | Robschlager | |
| 4,929,781 A | 5/1990 | James, Jr. et al. | |
| 4,939,310 A | 7/1990 | Wade | |
| 4,939,311 A | 7/1990 | Washecheck et al. | |
| 4,945,175 A | 7/1990 | Hobbs et al. | |
| 4,950,811 A | 8/1990 | Doussain et al. | |
| 4,950,822 A | 8/1990 | Dileo et al. | |
| 4,956,521 A | 9/1990 | Volles | |
| 4,962,252 A | 10/1990 | Wade | |
| 4,973,776 A | 11/1990 | Allenger et al. | |

| | | | | | |
|---|---|---|---|---|---|
| 4,973,786 A | 11/1990 | Karra | 5,334,777 A | 8/1994 | Miller et al. |
| 4,982,024 A | 1/1991 | Lin et al. | 5,345,021 A | 9/1994 | Casci et al. |
| 4,982,041 A | 1/1991 | Campbell | 5,354,916 A | 10/1994 | Horvath et al. |
| 4,988,660 A | 1/1991 | Campbell | 5,354,931 A | 10/1994 | Jan et al. |
| 4,990,696 A | 2/1991 | Stauffer | 5,366,949 A | 11/1994 | Schubert |
| 4,990,711 A | 2/1991 | Chen et al. | 5,371,313 A | 12/1994 | Ostrowicki |
| 5,001,293 A | 3/1991 | Nubel et al. | 5,382,704 A | 1/1995 | Krespan et al. |
| 5,004,847 A | 4/1991 | Beaver et al. | 5,382,743 A | 1/1995 | Beech, Jr. et al. |
| 5,013,424 A | 5/1991 | James, Jr. et al. | 5,382,744 A | 1/1995 | Abbott et al. |
| 5,013,793 A | 5/1991 | Wang et al. | 5,385,718 A | 1/1995 | Casci et al. |
| 5,019,652 A | 5/1991 | Taylor et al. | 5,395,981 A | 3/1995 | Marker |
| 5,026,934 A | 6/1991 | Bains et al. | 5,399,258 A | 3/1995 | Fletcher et al. |
| 5,026,937 A | 6/1991 | Bricker | 5,401,890 A | 3/1995 | Parks |
| 5,026,944 A | 6/1991 | Allenger et al. | 5,401,894 A | 3/1995 | Brasier et al. |
| 5,034,566 A | 7/1991 | Ishino et al. | 5,406,017 A | 4/1995 | Withers, Jr. |
| 5,043,502 A | 8/1991 | Martindale et al. | 5,414,173 A | 5/1995 | Garces et al. |
| 5,055,235 A | 10/1991 | Brackenridge et al. | 5,430,210 A | 7/1995 | Grasselli et al. |
| 5,055,633 A | 10/1991 | Volles | 5,430,214 A | 7/1995 | Smith et al. |
| 5,055,634 A | 10/1991 | Volles | 5,430,219 A | 7/1995 | Sanfilippo et al. |
| 5,059,744 A | 10/1991 | Harandi et al. | 5,436,378 A | 7/1995 | Masini et al. |
| 5,068,478 A | 11/1991 | Miller et al. | 5,444,168 A | 8/1995 | Brown |
| 5,071,449 A | 12/1991 | Sircar | 5,446,234 A | 8/1995 | Casci et al. |
| 5,071,815 A | 12/1991 | Wallace | 5,453,557 A | 9/1995 | Harley et al. |
| 5,073,656 A | 12/1991 | Chafin et al. | 5,456,822 A | 10/1995 | Marcilly et al. |
| 5,073,657 A | 12/1991 | Warren | 5,457,255 A | 10/1995 | Kumata et al. |
| 5,082,473 A | 1/1992 | Keefer | 5,464,799 A | 11/1995 | Casci et al. |
| 5,082,816 A | 1/1992 | Teller et al. | 5,465,699 A | 11/1995 | Voigt |
| 5,085,674 A | 2/1992 | Leavitt | 5,470,377 A | 11/1995 | Whitlock |
| 5,087,779 A | 2/1992 | Nubel et al. | 5,480,629 A | 1/1996 | Thompson et al. |
| 5,087,786 A | 2/1992 | Nubel et al. | 5,486,627 A | 1/1996 | Quarderer et al. |
| 5,087,787 A | 2/1992 | Kimble et al. | 5,489,719 A | 2/1996 | Le et al. |
| 5,093,542 A | 3/1992 | Gaffney | 5,489,727 A | 2/1996 | Randolph et al. |
| 5,096,469 A | 3/1992 | Keefer | 5,500,297 A | 3/1996 | Thompson et al. |
| 5,097,083 A | 3/1992 | Stauffer | 5,510,525 A | 4/1996 | Sen et al. |
| 5,099,084 A | 3/1992 | Stauffer | 5,523,503 A | 6/1996 | Funk et al. |
| 5,105,045 A | 4/1992 | Kimble et al. | 5,525,230 A | 6/1996 | Wrigley et al. |
| 5,105,046 A | 4/1992 | Washecheck | 5,538,540 A | 7/1996 | Whitlock |
| 5,107,032 A | 4/1992 | Erb et al. | 5,563,313 A | 10/1996 | Chung et al. |
| 5,107,051 A | 4/1992 | Pannell | 5,565,092 A | 10/1996 | Pannell et al. |
| 5,107,061 A | 4/1992 | Ou et al. | 5,565,616 A | 10/1996 | Li et al. |
| 5,108,579 A | 4/1992 | Casci | 5,571,762 A | 11/1996 | Clerici et al. |
| 5,118,899 A | 6/1992 | Kimble et al. | 5,571,885 A | 11/1996 | Chung et al. |
| 5,120,332 A | 6/1992 | Wells | 5,599,381 A | 2/1997 | Whitlock |
| 5,132,343 A | 7/1992 | Zwecker et al. | 5,600,043 A | 2/1997 | Johnston et al. |
| 5,138,112 A | 8/1992 | Gosling et al. | 5,600,045 A | 2/1997 | Van Der Aalst et al. |
| 5,139,991 A | 8/1992 | Taylor et al. | 5,609,654 A | 3/1997 | Le et al. |
| 5,146,027 A | 9/1992 | Gaffney | 5,633,419 A | 5/1997 | Spencer et al. |
| 5,157,189 A | 10/1992 | Karra | 5,639,930 A | 6/1997 | Penick |
| 5,160,502 A | 11/1992 | Kimble et al. | 5,653,956 A | 8/1997 | Zones |
| 5,166,452 A | 11/1992 | Gradl et al. | 5,656,149 A | 8/1997 | Zones et al. |
| 5,175,382 A | 12/1992 | Hebgen et al. | 5,661,097 A | 8/1997 | Spencer et al. |
| 5,178,748 A | 1/1993 | Casci et al. | 5,663,465 A | 9/1997 | Clegg et al. |
| 5,185,479 A | 2/1993 | Stauffer | 5,663,474 A | 9/1997 | Pham et al. |
| 5,188,725 A | 2/1993 | Harandi | 5,675,046 A | 10/1997 | Ohno et al. |
| 5,191,142 A | 3/1993 | Marshall et al. | 5,675,052 A | 10/1997 | Menon et al. |
| 5,194,244 A | 3/1993 | Brownscombe et al. | 5,679,134 A | 10/1997 | Brugerolle et al. |
| 5,202,506 A | 4/1993 | Kirchner et al. | 5,679,879 A | 10/1997 | Mercier et al. |
| 5,202,511 A | 4/1993 | Salinas, III et al. | 5,684,213 A | 11/1997 | Nemphos et al. |
| 5,210,357 A | 5/1993 | Kolts et al. | 5,693,191 A | 12/1997 | Pividal et al. |
| 5,215,648 A | 6/1993 | Zones et al. | 5,695,890 A | 12/1997 | Thompson et al. |
| 5,223,471 A | 6/1993 | Washecheck | 5,698,747 A | 12/1997 | Godwin et al. |
| 5,228,888 A | 7/1993 | Gmelin et al. | 5,705,712 A | 1/1998 | Frey et al. |
| 5,233,113 A | 8/1993 | Periana et al. | 5,705,728 A | 1/1998 | Viswanathan et al. |
| 5,237,115 A | 8/1993 | Makovec et al. | 5,705,729 A | 1/1998 | Huang |
| 5,243,098 A | 9/1993 | Miller et al. | 5,708,246 A | 1/1998 | Camaioni et al. |
| 5,243,114 A | 9/1993 | Johnson et al. | 5,720,858 A | 2/1998 | Noceti et al. |
| 5,245,109 A | 9/1993 | Kaminsky et al. | 5,728,897 A | 3/1998 | Buysch et al. |
| 5,254,772 A | 10/1993 | Dukat et al. | 5,728,905 A | 3/1998 | Clegg et al. |
| 5,254,790 A | 10/1993 | Thomas et al. | 5,734,073 A | 3/1998 | Chambers et al. |
| 5,264,635 A | 11/1993 | Le et al. | 5,741,949 A | 4/1998 | Mack |
| 5,268,518 A | 12/1993 | West et al. | 5,744,669 A | 4/1998 | Kalnes et al. |
| 5,276,226 A | 1/1994 | Horvath et al. | 5,750,801 A | 5/1998 | Buysch et al. |
| 5,276,240 A | 1/1994 | Timmons et al. | 5,770,175 A | 6/1998 | Zones |
| 5,276,242 A | 1/1994 | Wu | 5,776,871 A | 7/1998 | Cothran et al. |
| 5,284,990 A | 2/1994 | Peterson et al. | 5,780,703 A | 7/1998 | Chang et al. |
| 5,300,126 A | 4/1994 | Brown et al. | 5,798,314 A | 8/1998 | Spencer et al. |
| 5,306,855 A | 4/1994 | Periana et al. | 5,814,715 A | 9/1998 | Chen et al. |
| 5,316,995 A | 5/1994 | Kaminsky et al. | 5,817,904 A | 10/1998 | Vic et al. |
| 5,319,132 A | 6/1994 | Ozawa et al. | 5,821,394 A | 10/1998 | Schoebrechts et al. |

| | | |
|---|---|---|
| 5,847,224 A | 12/1998 | Koga et al. |
| 5,849,978 A | 12/1998 | Benazzi et al. |
| 5,866,735 A | 2/1999 | Cheung et al. |
| 5,895,831 A | 4/1999 | Brasier et al. |
| 5,898,086 A | 4/1999 | Harris |
| 5,905,169 A | 5/1999 | Jacobson |
| 5,906,892 A | 5/1999 | Thompson et al. |
| 5,908,963 A | 6/1999 | Voss et al. |
| 5,952,538 A | 9/1999 | Vaughn et al. |
| 5,959,170 A | 9/1999 | Withers |
| 5,968,236 A | 10/1999 | Bassine |
| 5,969,195 A | 10/1999 | Stabel et al. |
| 5,977,402 A | 11/1999 | Sekiguchi et al. |
| 5,983,476 A | 11/1999 | Eshelman et al. |
| 5,986,158 A | 11/1999 | Van Broekhoven et al. |
| 5,994,604 A | 11/1999 | Reagen et al. |
| 5,998,679 A | 12/1999 | Miller |
| 5,998,686 A | 12/1999 | Clem et al. |
| 6,002,059 A | 12/1999 | Hellring et al. |
| 6,015,867 A | 1/2000 | Fushimi et al. |
| 6,018,088 A | 1/2000 | Olah |
| 6,022,929 A | 2/2000 | Chen et al. |
| 6,034,288 A | 3/2000 | Scott et al. |
| 6,056,804 A | 5/2000 | Keefer et al. |
| 6,068,679 A | 5/2000 | Zheng |
| 6,072,091 A | 6/2000 | Cosyns et al. |
| 6,087,294 A | 7/2000 | Klabunde et al. |
| 6,090,312 A | 7/2000 | Ziaka et al. |
| 6,096,932 A | 8/2000 | Subramanian |
| 6,096,933 A | 8/2000 | Cheung et al. |
| 6,103,215 A | 8/2000 | Zones et al. |
| 6,107,561 A | 8/2000 | Thompson |
| 6,117,371 A | 9/2000 | Mack |
| 6,124,514 A | 9/2000 | Emmrich et al. |
| 6,127,588 A | 10/2000 | Kimble et al. |
| 6,130,260 A | 10/2000 | Hall et al. |
| 6,143,939 A | 11/2000 | Farcasiu et al. |
| 6,169,218 B1 | 1/2001 | Hearn et al. |
| 6,180,841 B1 | 1/2001 | Fatutto et al. |
| 6,187,871 B1 | 2/2001 | Thompson et al. |
| 6,187,983 B1 | 2/2001 | Sun |
| 6,203,712 B1 | 3/2001 | Bronner et al. |
| 6,207,864 B1 | 3/2001 | Henningsen et al. |
| 6,225,517 B1 | 5/2001 | Nascimento et al. |
| 6,248,218 B1 | 6/2001 | Linkous et al. |
| 6,265,505 B1 | 7/2001 | McConville et al. |
| 6,281,405 B1 | 8/2001 | Davis et al. |
| 6,320,085 B1 | 11/2001 | Arvai et al. |
| 6,337,063 B1 | 1/2002 | Rouleau et al. |
| 6,342,200 B1 | 1/2002 | Rouleau et al. |
| 6,368,490 B1 | 4/2002 | Gestermann |
| 6,369,283 B1 | 4/2002 | Guram et al. |
| 6,372,949 B1 | 4/2002 | Brown et al. |
| 6,376,731 B1 | 4/2002 | Evans et al. |
| 6,380,328 B1 | 4/2002 | McConville et al. |
| 6,380,423 B2 | 4/2002 | Banning et al. |
| 6,380,444 B1 | 4/2002 | Bjerrum et al. |
| 6,395,945 B1 | 5/2002 | Randolph |
| 6,403,840 B1 | 6/2002 | Zhou et al. |
| 6,406,523 B1 | 6/2002 | Connor et al. |
| 6,423,211 B1 | 7/2002 | Randolph et al. |
| 6,426,441 B1 | 7/2002 | Randolph et al. |
| 6,426,442 B1 | 7/2002 | Ichikawa et al. |
| 6,452,058 B1 | 9/2002 | Schweizer et al. |
| 6,455,650 B1 | 9/2002 | Lipian et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,345 B2 | 10/2002 | Hintermann et al. |
| 6,472,572 B1 | 10/2002 | Zhou et al. |
| 6,475,463 B1 | 11/2002 | Elomari et al. |
| 6,475,464 B1 | 11/2002 | Rouleau et al. |
| 6,479,705 B2 | 11/2002 | Murata et al. |
| 6,482,997 B2 | 11/2002 | Petit-Clair et al. |
| 6,486,368 B1 | 11/2002 | Zhou et al. |
| 6,495,484 B1 | 12/2002 | Holtcamp |
| 6,509,485 B2 | 1/2003 | Mul et al. |
| 6,511,526 B2 | 1/2003 | Jagger et al. |
| 6,514,319 B2 | 2/2003 | Keefer et al. |
| 6,518,474 B1 | 2/2003 | Sanderson et al. |
| 6,518,476 B1 | 2/2003 | Culp et al. |
| 6,525,228 B2 | 2/2003 | Chauvin et al. |
| 6,525,230 B2 | 2/2003 | Grosso |
| 6,528,693 B1 | 3/2003 | Gandy et al. |
| 6,538,162 B2 | 3/2003 | Chang et al. |
| 6,540,905 B1 | 4/2003 | Elomari |
| 6,545,191 B1 | 4/2003 | Stauffer |
| 6,547,958 B1 | 4/2003 | Elomari |
| 6,548,040 B1 | 4/2003 | Rouleau et al. |
| 6,552,241 B1 | 4/2003 | Randolph et al. |
| 6,566,572 B2 | 5/2003 | Okamoto et al. |
| 6,572,829 B2 | 6/2003 | Linkous et al. |
| 6,585,953 B2 | 7/2003 | Roberts et al. |
| 6,616,830 B2 | 9/2003 | Elomari |
| 6,620,757 B2 | 9/2003 | McConville et al. |
| 6,632,971 B2 | 10/2003 | Brown et al. |
| 6,635,793 B2 | 10/2003 | Mul et al. |
| 6,641,644 B2 | 11/2003 | Jagger et al. |
| 6,646,102 B2 | 11/2003 | Boriack et al. |
| 6,669,846 B2 | 12/2003 | Perriello |
| 6,672,572 B2 | 1/2004 | Werlen |
| 6,679,986 B1 | 1/2004 | Da Silva et al. |
| 6,680,415 B1 | 1/2004 | Gulotty, Jr. et al. |
| 6,692,626 B2 | 2/2004 | Keefer et al. |
| 6,692,723 B2 | 2/2004 | Rouleau et al. |
| 6,710,213 B2 | 3/2004 | Aoki et al. |
| 6,713,087 B2 | 3/2004 | Tracy et al. |
| 6,713,655 B2 | 3/2004 | Yilmaz et al. |
| RE38,493 E | 4/2004 | Keefer et al. |
| 6,723,808 B2 | 4/2004 | Holtcamp |
| 6,727,400 B2 | 4/2004 | Messier et al. |
| 6,740,146 B2 | 5/2004 | Simonds |
| 6,753,390 B2 | 6/2004 | Ehrman et al. |
| 6,765,120 B2 | 7/2004 | Weber et al. |
| 6,797,845 B1 | 9/2004 | Hickman et al. |
| 6,797,851 B2 | 9/2004 | Martens et al. |
| 6,821,924 B2 | 11/2004 | Gulotty, Jr. et al. |
| 6,822,123 B2 | 11/2004 | Stauffer |
| 6,822,125 B2 | 11/2004 | Lee et al. |
| 6,825,307 B2 | 11/2004 | Goodall |
| 6,825,383 B1 | 11/2004 | Dewkar et al. |
| 6,831,032 B2 | 12/2004 | Spaether |
| 6,838,576 B1 | 1/2005 | Wicki et al. |
| 6,841,063 B2 | 1/2005 | Elomari |
| 6,852,896 B2 | 2/2005 | Stauffer |
| 6,866,950 B2 | 3/2005 | Connor et al. |
| 6,869,903 B2 | 3/2005 | Matsunaga |
| 6,875,339 B2 | 4/2005 | Rangarajan et al. |
| 6,878,853 B2 | 4/2005 | Tanaka et al. |
| 6,888,013 B2 | 5/2005 | Paparatto et al. |
| 6,900,363 B2 | 5/2005 | Harth et al. |
| 6,902,602 B2 | 6/2005 | Keefer et al. |
| 6,903,171 B2 | 6/2005 | Rhodes et al. |
| 6,909,024 B1 | 6/2005 | Jones et al. |
| 6,921,597 B2 | 7/2005 | Keefer et al. |
| 6,933,417 B1 | 8/2005 | Henley et al. |
| 6,946,566 B2 | 9/2005 | Yaegashi et al. |
| 6,953,868 B2 | 10/2005 | Boaen et al. |
| 6,953,873 B2 | 10/2005 | Cortright et al. |
| 6,956,140 B2 | 10/2005 | Ehrenfeld |
| 6,958,306 B2 | 10/2005 | Holtcamp |
| 6,984,763 B2 | 1/2006 | Schweizer et al. |
| 7,001,872 B2 | 2/2006 | Pyecroft et al. |
| 7,002,050 B2 | 2/2006 | Santiago Fernandez et al. |
| 7,011,811 B2 | 3/2006 | Elomari |
| 7,019,182 B2 | 3/2006 | Grosso |
| 7,026,145 B2 | 4/2006 | Mizrahi et al. |
| 7,026,519 B2 | 4/2006 | Santiago Fernandez et al. |
| 7,037,358 B2 | 5/2006 | Babicki et al. |
| 7,045,670 B2 | 5/2006 | Johnson et al. |
| 7,049,388 B2 | 5/2006 | Boriack et al. |
| 7,053,252 B2 | 5/2006 | Boussand et al. |
| 7,057,081 B2 | 6/2006 | Allison et al. |
| 7,060,865 B2 | 6/2006 | Ding et al. |
| 7,064,238 B2 | 6/2006 | Waycuilis |
| 7,064,240 B2 | 6/2006 | Ohno et al. |
| 7,067,448 B1 | 6/2006 | Weitkamp et al. |
| 7,083,714 B2 | 8/2006 | Elomari |

| | | |
|---|---|---|
| 7,084,308 B1 | 8/2006 | Stauffer |
| 7,091,270 B2 | 8/2006 | Zilberman et al. |
| 7,091,387 B2 | 8/2006 | Fong et al. |
| 7,091,391 B2 | 8/2006 | Stauffer |
| 7,094,936 B1 | 8/2006 | Owens et al. |
| 7,098,371 B2 | 8/2006 | Mack et al. |
| 7,105,710 B2 | 9/2006 | Boons et al. |
| 7,138,534 B2 | 11/2006 | Forlin et al. |
| 7,141,708 B2 | 11/2006 | Marsella et al. |
| 7,145,045 B2 | 12/2006 | Harmsen et al. |
| 7,148,356 B2 | 12/2006 | Smith, III et al. |
| 7,148,390 B2 | 12/2006 | Zhou et al. |
| 7,151,199 B2 | 12/2006 | Martens et al. |
| 7,161,050 B2 | 1/2007 | Sherman et al. |
| 7,169,730 B2 | 1/2007 | Ma et al. |
| 7,176,340 B2 | 2/2007 | Van Broekhoven et al. |
| 7,176,342 B2 | 2/2007 | Bellussi et al. |
| 7,182,871 B2 | 2/2007 | Perriello |
| 7,193,093 B2 | 3/2007 | Murray et al. |
| 7,196,239 B2 | 3/2007 | Van Egmond et al. |
| 7,199,083 B2 | 4/2007 | Zevallos |
| 7,199,255 B2 | 4/2007 | Murray et al. |
| 7,208,641 B2 | 4/2007 | Nagasaki et al. |
| 7,214,750 B2 | 5/2007 | McDonald et al. |
| 7,220,391 B1 | 5/2007 | Huang et al. |
| 7,226,569 B2 | 6/2007 | Elomari |
| 7,226,576 B2 | 6/2007 | Elomari |
| 7,230,150 B2 | 6/2007 | Grosso et al. |
| 7,230,151 B2 | 6/2007 | Martens et al. |
| 7,232,872 B2 | 6/2007 | Shaffer et al. |
| 7,238,846 B2 | 7/2007 | Janssen et al. |
| 7,244,795 B2 | 7/2007 | Agapiou et al. |
| 7,244,867 B2 | 7/2007 | Waycuilis |
| 7,250,107 B2 | 7/2007 | Benazzi et al. |
| 7,250,542 B2 | 7/2007 | Smith, Jr. et al. |
| 7,252,920 B2 | 8/2007 | Kurokawa et al. |
| 7,253,327 B2 | 8/2007 | Janssens et al. |
| 7,253,328 B2 | 8/2007 | Stauffer |
| 7,265,193 B2 | 9/2007 | Weng et al. |
| 7,267,758 B2 | 9/2007 | Benazzi et al. |
| 7,268,263 B1 | 9/2007 | Frey et al. |
| 7,271,303 B1 | 9/2007 | Sechrist et al. |
| 7,273,957 B2 | 9/2007 | Bakshi et al. |
| 7,282,603 B2 | 10/2007 | Richards |
| 7,285,698 B2 | 10/2007 | Liu et al. |
| 7,304,193 B1 | 12/2007 | Frey et al. |
| 7,342,144 B2 | 3/2008 | Kaizik et al. |
| 7,348,295 B2 | 3/2008 | Zones et al. |
| 7,348,464 B2 | 3/2008 | Waycuilis |
| 7,357,904 B2 | 4/2008 | Zones et al. |
| 7,361,794 B2 | 4/2008 | Grosso |
| 7,390,395 B2 | 6/2008 | Elomari |
| 2002/0102672 A1 | 8/2002 | Mizrahi |
| 2002/0198416 A1 | 12/2002 | Zhou et al. |
| 2003/0004380 A1 | 1/2003 | Grumann |
| 2003/0065239 A1 | 4/2003 | Zhu |
| 2003/0069452 A1 | 4/2003 | Sherman et al. |
| 2003/0078456 A1 | 4/2003 | Yilmaz et al. |
| 2003/0120121 A1 | 6/2003 | Sherman et al. |
| 2003/0125589 A1 | 7/2003 | Grosso |
| 2003/0166973 A1 | 9/2003 | Zhou et al. |
| 2004/0006246 A1 | 1/2004 | Sherman et al. |
| 2004/0062705 A1 | 4/2004 | Leduc |
| 2004/0152929 A1 | 8/2004 | Clarke |
| 2004/0158107 A1 | 8/2004 | Aoki |
| 2004/0158108 A1 | 8/2004 | Snoble |
| 2004/0187684 A1 | 9/2004 | Elomari |
| 2005/0047927 A1 | 3/2005 | Lee et al. |
| 2005/0148805 A1 | 7/2005 | Jones |
| 2005/0171393 A1 | 8/2005 | Lorkovic |
| 2005/0192468 A1 | 9/2005 | Sherman et al. |
| 2005/0215837 A1 | 9/2005 | Hoffpauir |
| 2005/0234276 A1 | 10/2005 | Waycuilis |
| 2005/0245772 A1 | 11/2005 | Fong |
| 2005/0245777 A1 | 11/2005 | Fong |
| 2005/0267224 A1 | 12/2005 | Herling |
| 2006/0025617 A1 | 2/2006 | Begley |
| 2006/0100469 A1 | 5/2006 | Waycuilis |
| 2006/0135823 A1 | 6/2006 | Jun |
| 2006/0138025 A1 | 6/2006 | Zones |
| 2006/0138026 A1 | 6/2006 | Chen |
| 2006/0149116 A1 | 7/2006 | Slaugh |
| 2006/0229228 A1 | 10/2006 | Komon et al. |
| 2006/0229475 A1 | 10/2006 | Weiss et al. |
| 2006/0270863 A1 | 11/2006 | Reiling |
| 2006/0288690 A1 | 12/2006 | Elomari |
| 2007/0004955 A1 | 1/2007 | Kay |
| 2007/0078285 A1 | 4/2007 | Dagle |
| 2007/0100189 A1 | 5/2007 | Stauffer |
| 2007/0129584 A1 | 6/2007 | Basset |
| 2007/0142680 A1 | 6/2007 | Ayoub |
| 2007/0148067 A1 | 6/2007 | Zones |
| 2007/0148086 A1 | 6/2007 | Zones |
| 2007/0149778 A1 | 6/2007 | Zones |
| 2007/0149789 A1 | 6/2007 | Zones |
| 2007/0149819 A1 | 6/2007 | Zones |
| 2007/0149824 A1 | 6/2007 | Zones |
| 2007/0149837 A1 | 6/2007 | Zones |
| 2007/0197801 A1 | 8/2007 | Bolk |
| 2007/0197847 A1 | 8/2007 | Liu |
| 2007/0213545 A1 | 9/2007 | Bolk |
| 2007/0238905 A1 | 10/2007 | Arredondo |
| 2007/0238909 A1 | 10/2007 | Gadewar et al. |
| 2007/0251382 A1 | 11/2007 | Gadewar |
| 2007/0276168 A1 | 11/2007 | Garel |
| 2007/0284284 A1 | 12/2007 | Zones |
| 2008/0171898 A1 | 7/2008 | Waycuilis |
| 2008/0183022 A1 | 7/2008 | Waycuilis |
| 2008/0188697 A1 | 8/2008 | Lorkovic |
| 2008/0269534 A1 | 10/2008 | Lorkovic |
| 2008/0314758 A1 | 12/2008 | Grosso |
| 2009/0069606 A1 | 3/2009 | Komon |
| 2009/0127163 A1 | 5/2009 | Weiss |
| 2010/0096588 A1 | 4/2010 | Gadewar |
| 2010/0099928 A1 | 4/2010 | Gadewar |
| 2010/0099929 A1 | 4/2010 | Gadewar |
| 2010/0099930 A1 | 4/2010 | Stoimenov |
| 2010/0121119 A1 | 5/2010 | Sherman |

FOREIGN PATENT DOCUMENTS

| | | |
|---|---|---|
| CA | 1099656 | 4/1981 |
| CA | 1101441 | 5/1981 |
| CA | 1202610 | 4/1986 |
| CA | 2447761 A1 | 11/2002 |
| CA | 2471295 A1 | 7/2003 |
| CA | 2542857 | 5/2005 |
| CA | 2236126 | 8/2006 |
| CA | 2203115 | 9/2006 |
| CA | 2510093 | 12/2006 |
| EP | 0021497 | 1/1981 |
| EP | 0164798 A1 | 12/1985 |
| EP | 0418971 A1 | 3/1991 |
| EP | 0418974 A1 | 3/1991 |
| EP | 0418975 A1 | 3/1991 |
| EP | 0510238 A1 | 10/1992 |
| EP | 0526908 A2 | 2/1993 |
| EP | 0346612 B1 | 8/1993 |
| EP | 0560546 A1 | 9/1993 |
| EP | 0976705 A1 | 7/1998 |
| EP | 1186591 A2 | 3/2002 |
| EP | 1253126 A1 | 10/2002 |
| EP | 1312411 A2 | 5/2003 |
| EP | 1395536 | 3/2004 |
| EP | 1404636 | 4/2004 |
| EP | 1235769 B1 | 5/2004 |
| EP | 1435349 A2 | 7/2004 |
| EP | 1440939 A1 | 7/2004 |
| EP | 1474371 | 11/2004 |
| EP | 1235772 B1 | 1/2005 |
| EP | 1661620 A1 | 5/2006 |
| EP | 1760057 A1 | 3/2007 |
| EP | 1689728 B1 | 4/2007 |
| EP | 1808227 A1 | 7/2007 |
| EP | 1837320 A1 | 9/2007 |
| GB | 5125 | 2/1912 |
| GB | 156122 | 3/1922 |
| GB | 294100 | 6/1929 |
| GB | 363009 | 12/1931 |

| | | |
|---|---|---|
| GB | 402928 | 12/1933 |
| GB | 474922 A | 11/1937 |
| GB | 536491 | 5/1941 |
| GB | 553950 | 6/1943 |
| GB | 586483 | 3/1947 |
| GB | 775590 | 5/1957 |
| GB | 793214 | 4/1958 |
| GB | 796048 | 6/1958 |
| GB | 796085 | 6/1958 |
| GB | 883256 | 11/1961 |
| GB | 950975 | 3/1964 |
| GB | 950976 | 3/1964 |
| GB | 991303 | 5/1965 |
| GB | 995960 | 6/1965 |
| GB | 1015033 | 12/1965 |
| GB | 1104294 | 2/1968 |
| GB | 1133752 | 11/1968 |
| GB | 1172002 | 11/1969 |
| GB | 1212240 | 11/1970 |
| GB | 1233299 | 5/1971 |
| GB | 1253618 | 11/1971 |
| GB | 1263806 A | 2/1972 |
| GB | 1446803 | 8/1976 |
| GB | 1542112 | 3/1979 |
| GB | 2095243 A | 9/1982 |
| GB | 2095245 A | 9/1982 |
| GB | 2095249 A | 9/1982 |
| GB | 2116546 A | 9/1982 |
| GB | 2120249 A | 11/1983 |
| GB | 2185754 A | 7/1987 |
| GB | 2191214 A | 12/1987 |
| JP | 2004-529189 | 9/2004 |
| WO | 83/00859 | 3/1983 |
| WO | 85/04863 | 11/1985 |
| WO | 85/04867 | 11/1985 |
| WO | 90/08120 | 7/1990 |
| WO | 90/08752 | 8/1990 |
| WO | 91/18856 | 12/1991 |
| WO | 92/03401 | 3/1992 |
| WO | 92/12946 | 8/1992 |
| WO | 93/16798 | 9/1993 |
| WO | 96/22263 | 7/1996 |
| WO | 97/44302 | 11/1997 |
| WO | 98/12165 | 3/1998 |
| WO | 99/07443 | 2/1999 |
| WO | 00/07718 A1 | 2/2000 |
| WO | 00/09261 A1 | 2/2000 |
| WO | 01/14300 A1 | 3/2001 |
| WO | 01/38275 A1 | 5/2001 |
| WO | 01/44149 A1 | 6/2001 |
| WO | 02/094749 A1 | 11/2002 |
| WO | 02/094750 A1 | 11/2002 |
| WO | 02/094751 A2 | 11/2002 |
| WO | 02/094752 A1 | 11/2002 |
| WO | 03/000635 A1 | 1/2003 |
| WO | 03/002251 A2 | 1/2003 |
| WO | 03/018524 A1 | 3/2003 |
| WO | 03/020676 A1 | 3/2003 |
| WO | 03/022827 A1 | 3/2003 |
| WO | 03/043575 A2 | 5/2003 |
| WO | 03/051813 A1 | 6/2003 |
| WO | 03/062143 A1 | 7/2003 |
| WO | 03/062172 A2 | 7/2003 |
| WO | 03/078366 A1 | 9/2003 |
| WO | 2004/018093 A2 | 3/2004 |
| WO | 2004/067487 A2 | 8/2004 |
| WO | 2005/014168 A1 | 2/2005 |
| WO | 2005/019143 A1 | 3/2005 |
| WO | 2005/021468 | 3/2005 |
| WO | 2005/021468 A1 | 3/2005 |
| WO | 2005/035121 A2 | 4/2005 |
| WO | 2005/037758 A1 | 4/2005 |
| WO | 2005/054120 A2 | 6/2005 |
| WO | 2005/056525 A2 | 6/2005 |
| WO | 2005/058782 A1 | 6/2005 |
| WO | 2005/090272 A1 | 9/2005 |
| WO | 2005/095310 A2 | 10/2005 |
| WO | 2005/105709 A1 | 11/2005 |
| WO | 2005/105715 A1 | 11/2005 |
| WO | 2005/110953 A1 | 11/2005 |
| WO | 2005/113437 A1 | 12/2005 |
| WO | 2005/113440 A1 | 12/2005 |
| WO | 2006/007093 A1 | 1/2006 |
| WO | 2006/015824 A1 | 2/2006 |
| WO | 2006/019399 A2 | 2/2006 |
| WO | 2006/020234 A1 | 2/2006 |
| WO | 2006/036293 A1 | 4/2006 |
| WO | 2006/039213 A1 | 4/2006 |
| WO | 2006/039354 A2 | 4/2006 |
| WO | 2006/043075 A1 | 4/2006 |
| WO | 2006/053345 A1 | 5/2006 |
| WO | 2006-067155 A2 | 6/2006 |
| WO | 2006/067188 A | 6/2006 |
| WO | 2006/067190 A1 | 6/2006 |
| WO | 2006/067191 A1 | 6/2006 |
| WO | 2006/067192 A | 6/2006 |
| WO | 2006/067193 A1 | 6/2006 |
| WO | 2006/069107 A2 | 6/2006 |
| WO | 2006/071354 A1 | 7/2006 |
| WO | 2006/076942 A1 | 7/2006 |
| WO | 2006/083427 A1 | 8/2006 |
| WO | 2006-100312 A2 | 9/2006 |
| WO | 2006/104909 A2 | 10/2006 |
| WO | 2006/104914 | 10/2006 |
| WO | 2006/104914 A1 | 10/2006 |
| WO | 2006/111997 A1 | 10/2006 |
| WO | 2006/113205 A2 | 10/2006 |
| WO | 2006/118935 A2 | 11/2006 |
| WO | 2007/001934 A2 | 1/2007 |
| WO | 2007/017900 A2 | 2/2007 |
| WO | 2007/044139 A1 | 4/2007 |
| WO | 2007/046986 A2 | 4/2007 |
| WO | 2007/050745 A1 | 5/2007 |
| WO | 2007/071046 A1 | 6/2007 |
| WO | 2007/079038 A2 | 7/2007 |
| WO | 2007/091009 A2 | 8/2007 |
| WO | 2007/094995 A2 | 8/2007 |
| WO | 2007/107031 A1 | 9/2007 |
| WO | 2007/111997 A2 | 10/2007 |
| WO | 2007/114479 A1 | 10/2007 |
| WO | 2007/125332 A1 | 11/2007 |
| WO | 2007/130054 A1 | 11/2007 |
| WO | 2007/130055 A1 | 11/2007 |
| WO | 2007/141295 A1 | 12/2007 |
| WO | 2007/142745 A1 | 12/2007 |
| WO | 2008/036562 | 3/2008 |
| WO | 2008/036563 | 3/2008 |
| WO | 2008/106319 | 9/2008 |
| WO | 2008/157043 | 12/2008 |
| WO | 2008/157044 | 12/2008 |
| WO | 2008/157045 | 12/2008 |
| WO | 2008/157046 | 12/2008 |
| WO | 2008/157047 | 12/2008 |

OTHER PUBLICATIONS

U.S. Appl. No. 60/559,844, filed Apr. 6, 2004, Sherman et al.
U.S. Appl. No. 60/765,115, filed Feb. 3, 2006, Gadewar et al.
Abstract of JP2007045756, Hydrogenation method using diaphragm type hydrogenation catalyst, hydrogenation reaction apparatus and diaphragm type hydrogenation catalyst, Publication date: Feb. 22, 2007, Inventor: Shuji et al., esp@cenet database—worldwide.
Abstract of JP2007061594, Method for decomposing organohalogen compound and mobile decomposition system, Publication date: Mar. 15, 2007, Inventor: Koichi et al., esp@cenet database—worldwide.
Abstract of JP2007099729, Method for producing alpha-methylstyrene or cumene, Publication date: Apr. 19, 2007, Inventor: Toshio, esp@cenet database—worldwide.
Abstract of RO119778, Process for preparing perchloroethylene, Publication date: Mar. 30, 2005, Inventor: Horia et al., esp@cenet database—worldwide.
Abstract of WO0105737; Method for preparing a carboxylic acid, Publication date: Jan. 25, 2001, Inventor: Pascal et al., esp@cenet database—worldwide.
Abstract of WO0105738, Method for preparing a carboxylic acid, Publication date: Jan. 25, 2001, Inventor: Pascal et al., esp@cenet database—worldwide.

Abstract of WO2004092099, Method for producing cyclic enols, Publication date: Oct. 28, 2004, Inventor: Marko et al., esp@cenet database—worldwide.
Abstract of WO2006063852, Electroluminescent polymers and use thereof, Publication date: Jun. 22, 2006, Inventor: Arne et al., esp@cenet database—worldwide.
Abstract of WO2006136135, Method for decarboxylating C-C cross-linking of carboxylic acids with carbon electrophiles, Publication date: Dec. 28, 2006, Inventor: Goossen Lukas et al., esp@cenet database—worldwide.
Abstract of WO2007028761, Method for chlorinating alcohols, Publication date: Mar. 15, 2007, Inventor: Rohde et al., esp@cenet database—worldwide.
Abstract of WO2007128842, Catalytic transalkylation of dialkyl benzenes, Publication date: Nov. 15, 2007, Inventor: Goncalvesalmeida et al., esp@cenet database—worldwide.
Abstract of WO2007137566, Method for catalytic conversion of organic oxygenated compounds from biomaterials, Publication date: Dec. 6, 2007, Inventor: Reschetilowski, esp@cenet database—worldwide.
Abstract of WO9721656, Method for making fluoroalkanols, Publication date: Jun. 19, 1997, Inventor Gillet, esp@cenet database—worldwide.
Abstract of WO9950213, Method for producing dialkyl ethers, Publication date: Oct. 7, 1999, Inventor: Falkowski Juergen et al., esp@cenet database—worldwide.
Adachi, et al.; Synthesis of Sialyl Lewis X Ganglioside Analogs Containing a Variable Length Spacer Between the Sugar and Lipophilic Moieties; J. Carbohydrate Chem., vol. 17, No. 4-5, (1998), pp. 595-607, XP009081720.
Abstract of EP0039471, Process for the preparation of 2-chloro-1,1,1,.2,3,3,3-heptafluoropropane, Publication date: Nov. 11, 1981, Inventor: Von Halasz, esp@cenet database—worldwide.
Abstract of EP0101337, Process for the production of methylene chloride, Publication date: Feb. 22, 1984, Inventor: Olah et al., esp@cenet database—worldwide.
Abstract of EP0407989, Method for the production of 1,1,1-trifluoro-2;2-dichloroethane by photochlorination, Publication date: Jan. 16, 1991, Inventor: Cremer et al., esp@cenet database—worldwide.
Abstract of EP0442258, Process for the preparation of a polyunsaturated olefin, Publication date: Aug. 21, 1991, Inventor: Gaudin et al., esp@cenet database—worldwide.
Abstract of EP0465294, Process for the preparation of unsaturated bromides, Publication date: Jan. 8, 1992, Inventor: Decaudin et al., esp@cenet database—worldwide.
Abstract of EP0549387, Synthesis of n-perfluorooctylbromide, Publication date: Jun. 30, 1993, Inventor: Drivon et al., esp@cenet database—worldwide.
Abstract of EP0850906, Process and apparatus for the etherification of olefinic hydrocarbon feedstocks, Publication date: Jul. 1, 1998, Inventor: Masson, esp@cenet database—worldwide.
Abstract of EP0858987, Process for the conversion of lighter alkanes to higher hydrocarbons, Publication date: Aug. 19, 1998, Inventor: Amariglio et al., esp@cenet database—worldwide.
Bakker, et al.; An Exploratory Study of the Addition Reaction of Ethyleneglcol, 2-Chloroethanlo and 1, 3-Dichloro-2-Propanol to 1-Dodecene; J. Am. Oil Chem. Soc., vol. 44, No. 9 (1967), pp. 517-521; XP009081570.
Abstract of EP0235110, Process for the stabilization of silicalite catalysts, Publication date: Sep. 2, 1987, Inventor: Debras et al., esp@cenet database—worldwide.
Bouzide et al.; Highly Selective Silver (I) Oxide Mediated Monoprotection of Symmetricl Diols; Tetrahedron Letters, Elsevier, vol. 38, No. 34 (1997), pp. 5945-5948; XP004094157.
Combined International Search Report and Written Opinion Dated Apr. 17, 2007 for PCT/US06/13394, in the name of GRT.
Gibson; Phase-Transfer Synthesis of Monoalkyl Ethers of Oligoethylene Glycols; Journal of Organic Chemistry, vol. 45, No. 6 (1980) pp. 1095-1098; XP002427776.
Klabunde, Kenneth J., et al., Changes in Texture and Catalytic Activity of Nanocrystalline MgO during Its Transformation to MgC12 in the Reaction with 1-Chlorobutane, J. Phys. Chem. B 2001, 105, 3937-3941.

Loiseau et al.; Multigram Synthesis of Well-Defined Extended Bifunctional Polyethylene Glycol (PEG) Chains; J. of Organic Chem., vol. 69, No. 3 (2004), pp. 639-647; XP002345040.
Mihai et al.; Application of Bronsted-type LFER in the study of phospholipase C mechanism; J. Am. Chem. Soc., vol. 125, No. 11 (2003) pp. 3236-3242; XP002427799.
Motupally et al., Recycling Chlorine from Hydrogen Chloride: A New and Economical Electrolytic Process, The Electrochemical Society Interface, Fall 1998.
Nishikawa et al.; Ultrasonic Relaxations in Aqueous Solutions of Alcohols and the Balance Between Hydrophobicity and Hydrophilicity of the Solutes; J. Phys. Chem. vol. 97, No. 14 (1993), pp. 3539-3544; XP002427775.
Prelog et al.; Chirale 2,2'-Polyoxaalkano-9,9'-Spirobifluorene; Helvetica Chimica ACTA, vol. 62, No. 7, (1979) pp. 2285-2302; XP002030901.
Shimizu et al., Gas-Phase Electrolysis of Hydrobromic Acid Using PTFE-Bonded Carbon Eletrode, Int. J. Hydrogen Energy, vol. 13, No. 6. pp. 345-349, 1988.
Velzen et al., HBr Electrolysis in the Ispra Mark 13A Flue Gas Desulphurization Process: Electrolysis in a DEM Cell, J. of Applied Electrochemistry, vol. 20, pp. 60-68, 1990.
Whitesides et al.; Nuclear Magnetic Resonance Spectroscopy. The Effect of Structure on Magnetic Nonequivalence Due to Molecular Asymmetry; J. Am. Chem. Soc., vol. 86, No. 13 (1964), pp. 2628-2634; XP002427774.
JLM Technology Ltd.; "The Miller GLS Technology for Conversion of Light Hydrocarbons to Alcohols"; New Science for the Benefit of Humanity; May 31, 2000; pp. 1-10.
Jaumain, Denis and Su, Bao-Lian; "Direct Catalytic Conversion of Chloromethane to Higher Hydrocarbons Over Various Protonic and Cationic Zeolite Catalysts as Studied by in-situ FTIR and Catalytic Testing"; 2000; pp. 1607-1612; Studies in Surface Science and Catalysis 130; Elsevier Science B.V.
Taylor, Charles E.; "Conversion of Substituted Methanes Over ZSM-Catalysts"; 2000; pp. 3633-3638; Studies in Surface Science and Catalysis 130; Elsevier Science B.V.
ZSM-5 Catalyst; http://chemelab.ucsd.edu/methanol/memos/ZSM-5.html; Nov. 6, 2003; p. 1.
Final Report; "Abstract"; http://chemelab.ucsd.edu/methanol/memos/final.html; May 9, 2004; pp. 1-7.
Driscoll, Daniel J.; "Direct Methane Conversion"; Federal Energy Technology Center, U.S. Department of Energy; M970779; 2001; pp. 1-10.
Olah et al.; "Selective Monohalogenation of Methane over Supported Abid or Platinum Metal Catalysts and Hydrolysis of Methyl Halides . . . "; J. American Chemical Society 1985, vol. 107; 0002-7863/85/1507-7097$01.50/0; pp. 7097-7105.
Murray et al.; "Conversion of Methyl Halides to Hydrocarbons on Basic Zeolites: A Discovery by in Situ NMR"; J. American Chemical Society 1993, vol. 115; pp. 4732-4741.
Lorkovic et al.; "A Novel Integrated Process for the Functionalization of Methane and Ethane: Bromine as Mediator", Catalysis Today 98; 2004; pp. 317-322.
Lorkovic et al.; "C1 Oxidative Coupling via Bromine Activation and Tandem Catalytic Condensation over CaO/ Zeolite Composites II . . . "; Catalysis Today 98; 2004; pp. 589-594.
Olah et al.; "Antimony Pentafluoride/Graphite Catalyzed Oxidative Conversion of Methyl Halides with Copper Oxides (or Copper/Oxygen) to Dimethyl Ether"; J. Org. Chem. 1990, 55; 1990 American Chemical Society; pp. 4289-4293.
Taylor, Charles E. et al.; "Direct Conversion of Methane to Liquid Hydrocarbons Through Chlorocarbon Intermediates"; 1988 Elsevier Science Publishers B.V. Amsterdam, Netherlands; pp. 483-489.
Chang, Clarence D. et al.; "The Conversion of Methanol and Other O-Compounds to Hydrocarbons over Zeolite Catalysts"; Journal of Catalysis 47; 1977; Academic Press, Inc.; pp. 249-259.
Zhou, Xiao-Ping et al.; "An Integrated Process for Partial Oxidation of Alkanes"; Chem. Commun. 2003; The Royal Society of Chemistry 2003; pp. 2294-2295.
Sun, Shouli et al.; "A General Integrated Process for Synthesizing Olefin Oxides"; Chem. Commun. 2004; The Royal Society of Chemistry 2004; pp. 2100-2101.

Lorkovic, Ivan M. et al.; "C1 Oxidative Coupling via Bromine Activation and Tandem Catalytic Condensation and Neutralization over CaO/Zeolite Composites II . . . "; Catalysis Today 98; 2004; pp. 589-594.

Yilmaz, Aysen et al.; "Bromine Mediated Partial Oxidation of Ethane over Nanostructured Zirconia Supported Metal Oxide/Bromide"; Microporous and Mesoporous Materials, 79; 2005; pp. 205-214.

Taylor, Charles E.; "PETC's On-Site Natural Gas Conversion Efforts"; Preprints of the Fuel Division, 208th National Meeting of the American Chemical Society, 39 (4); 1994; pp. 1228-1232.

Ione et al.; "Syntheses of Hydrocarbons from Compounds Containing One Carbon Atom Using Bifunctional Zeolite Catalysts"; Solid Fuel Chemistry (Khimiya Tverdogo Topliva); 1982; pp. 29-43; vol. 16, No. 6; Allerton Press. Inc.

Olah, George A. et al.; "Hydrocarbons Through Methane Derivatives"; Hydrocarbon Chemistry; 1995; pp. 89-90; John Wiley & Sons, Inc.

Akhrem, Irena S. et al.; "Ionic Bromination of Ethane and Other Alkanes (Cycloalkanes) with Bromine Catalyzed by the Polyhalomethane-2AlBr3 Aprotic Organic Superacids Under Mild Conditions"; Tetrahedron Letters, vol. 36, No. 51, 1995; pp. 9365-9368; Pergamon; Great Britain.

Smirnov, Vladimir V. et al.; "Selective Bromination of Alkanes and Arylalkanes with CBr4"; Mendeleev Commun. 2000; pp. 175-176.

Olah, George A.; "Electrophilic Methane Conversion"; Acc. Chem. Res. 1987, 20; pp. 422-428; American Chemical Society, Loker Hydrocarbon Research Institute and Dept. of Chemistry; University of Southern California.

Olah, George A. et al.; "Antimony Pentafluoride/Graphite Catalyzed Oxidative Carbonylation of Methyl Halides with Carbon Monoxide and Copper Oxides (or Copper/Oxygen) to Methyl Acetate"; J. Org. Chem. 1990, 55; pp. 4293-4297; Loker Hydrocarbon Research Institute and Dept. of Chemistry; University of Southern California.

Bagno, Alessandro et al.; "Superacid-Catalyzed Carbonylation of Methane, Methyl Halides, Methyl Alcohol, and Dimethyl Ether to Methyl Acetate and Acetic Acid"; J. Org. Chem. 1990, 55; pp. 4284-4289; Loker Hydrocarbon Research Institute; University of Southern California.

Olah, George A. et al.; "Onium Ylide Chemistry. 1. Bifunctional Acid-Base-Catalyzed Conversion of Heterosubstituted Methanes into Ethylene and Derived Hydrocarbons. The Onium Ylide Mechanism of the C1-C2 Conversion"; J. Am. Chem. Soc. 1984, 106; pp. 2143-2149.

Mochida, Isao et al.; "The Catalytic Dehydrohalogenation of Haloethanes on Solid Acids and Bases"; Bulletin of the Chemical Society of Japan, vol. 44; 1971; pp. 3305-3310.

Richards, Ryan et al.; "Nanocrystalline Ultra High Surface Area Magnesium Oxide as a Selective Base Catalyst"; Scripta Materialia, 44; 2001; pp. 1663-1666; Elsevier Science Ltd.

Sun, Naijian et al.; "Nanocrystal Metal Oxide—Chlorine Adducts: Selective Catalysts for Chlorination of Alkanes"; J. Am. Chem. Soc. 1999, 121; pp. 5587-5588; American Chemical Society.

Mishakov, Ilya V. et al.; "Nanocrystalline MgO as a Dehydrohalogenation Catalyst"; Journal of Catalysis 206; 2002; pp. 40-48; Elsevier Science, USA.

Wagner, George W. et al.; "Reactions of VX, GD, and HD with Nanosize CaO: Autocatalytic Dehydrohalogenation of HD"; J. Phys. Chem. B 2000, 104; pp. 5118-5123; 2000 American Chemical Society.

Fenelonov, Vladimir B. et al.; "Changes in Texture and Catalytic Activity of Nanocrystalline MgO during Its Transformation to MgCl2 in the Reaction with 1-Chlorobutane"; J. Phys. Chem. B 2001, 105; pp. 3937-3941; 2001 American Chemical Society.

http://webbook.nist.gov/; "Welcome to the NIST Chemistry WebBook"; 2005; U.S. Secretary of Commerce on Behalf of the United States of America.

Claude, Marion C. et al.; "Monomethyl-Branching of Long n-Alkanes in the Range from Decane to Tetracosane on Pt/H-ZSM-22 Bifunctional Catalyst"; Journal of Catalysis 190; 2000; pp. 39-48.

Thomas, J. M. et al.; "Synthesis and Characterization of a Catalytically Active Nickel-Silicoaluminophosphate Catalyst for the Conversion of Methanol to Ethene"; Chem. Mater.; 1991, 3; pp. 667-672; 1991 American Chemical Society.

Thomas, John Meurig et al.; "Catalytically Active Centres in Porous Oxides: Design and Performance of Highly Selective New Catalysts"; Chem. Commun.; 2001; pp. 675-687.

Lorkovic, Ivan et al.; "C1 Coupling via Bromine Activation and Tandem Catalytic Condensation and Neutralization over CaO/Zeolite Composites"; Chem. Commun., 2004; pp. 566-567.

Tamura, Masuhiko et al.; "The Reactions of Grignard Reagents with Transition Metal Halides: Coupling, Disproportionation, and Exchange with Olefins"; Bulletin of the Chemical Society of Japan, vol. 44.; Nov. 1971; pp. 3063-3073.

Weissermel, Klaus et al.; "Industrial Organic Chemistry"; 3rd Edition 1997. pp. 160-162, and 208.

Abstract of BE812868, Aromatic hydrocarbons prodn. from chlorinated hydrocarbons, Publication date: Sep. 27, 1974, esp@cenet database—worldwide.

Abstract of BE814900, Volatile aramatic cpds. prodn., Publication date: Sep. 2, 1974, esp@cenet database—worldwide.

Abstract of CN1199039, Pentanol and its production process, Publication date: Nov. 18, 1998, Inventor: Kailun, esp@cenet database—worldwide.

Abstract of CN1210847, Process for producing low carbon alcohol by directly hydrating low carbon olefines, Publication date: Mar. 17, 1999, Inventor: Zhenguo et al., esp@cenet database—worldwide.

Abstract of CN1321728, Method for preparing aromatic hydrocarbon and hydrogen gas by using low-pressure gas, Publication date: Nov. 14, 2001, Inventor: Jie et al., esp@cenet database—worldwide.

Abstract of CN1451721, Process for non-catalytic combustion deoxidizing coal mine gas for producing methanol, Publication date: Oct. 29, 2003, Inventor: Pengwan et al., esp@cenet database—worldwide.

Abstract of CN1623969, Method for preparing 1, 4-benzene dimethanol, Publication date: Jun. 8, 2005, Inventor: Jiarong et al., esp@cenet database—worldwide.

Abstract of CN1657592, Method for converting oil to multiple energy fuel product, Publication date: Aug. 24, 2005, Inventor: Li, esp@cenet database—worldwide.

Abstract of CN1687316, Method for producing biologic diesel oil from rosin, Publication date: Oct. 26, 2005, Inventor: Jianchun et al., esp@cenet database—worldwide.

Abstract of CN1696248, Method for synthesizing biologic diesel oil based on ion liquid, Publication date: Nov. 16, 2005, Inventor: Sun, esp@cenet database—worldwide.

Abstract of CN1699516, Process for preparing bio-diesel-oil by using microalgae fat, Publication date: Nov. 23, 2005, Inventor: Miao, esp@cenet database—worldwide.

Abstract of CN1704392, Process for producing alkylbenzene, Publication date: Dec. 7, 2005, Inventor: Gao, esp@cenet database—worldwide.

Abstract of CN1724612, Biological diesel oil catalyst and method of synthesizing biological diesel oil using sai catalyst, Publication date: Jan. 25, 2006, Inventor: Gu, esp@cenet database—worldwide.

Abstract of CN1986737, Process of producing biodiesel oil with catering waste oil, Publication date: Jun. 27, 2007, Inventor: Chen, esp@cenet database—worldwide.

Abstract of CN100999680, Esterification reaction tech. of preparing biodiesel by waste oil, Publication date: Jul. 18, 2007, Inventor: Weiming, esp@cenet database—worldwide.

Abstract of CN101016229, Refining method for bromomeoamyl alcohol, Publication date: Aug. 15, 2007, Inventor: Tian, esp@cenet database—worldwide.

Abstract of DE3209964, Process for the preparation of chlorinated hydrocarbons, Publication date: Nov. 11, 1982, Inventor: Pyke et al., esp@cenet database—worldwide.

Abstract of DE3210196, Process for the preparation of a monochlorinated olefin, Publication date: Jan. 5, 1983, Inventor: Pyke et al., esp@cenet database—worldwide.

Abstract of DE3226028, Process for the preparation of monochlorinated olefin, Publication date: Feb. 3, 1983, Inventor: Pyke et al., esp@cenet database—worldwide.

Abstract of DE3334225, Process for the preparation of 1, 2-dichloroethane, Publication date: Apr. 4, 1985, Inventor: Hebgen et al., esp@cenet database—worldwide.

Abstract of DE4232056, 2,5-Di:methyl-hexane-2, 5-di:ol continuous prodn. from tert. butanol—by oxidative dimerisation in two phase system with vigorous stirring, using aq. phase with specified density to facilitate phase sepn., Publication date: Mar. 31, 1994, Inventor: Gnann et al., esp@cenet database—worldwide.

Abstract of DE4434823, Continuous prodn. of hydroxy-benzyl alkyl ether, Publication date: Apr. 4, 1996, Inventor: Stein et al., esp@cenet database—worldwide.

Abstract of FR2692259, Aromatisation of 2-4C hydrocarbons—using a fixed-mobile-catalytic bed process, Publication date: Dec. 17, 1993, Inventor: Alario et al., esp@cenet database—worldwide.

Abstract of FR2880019, Manufacturing 1, 2-dichloroethane, comprises cracking core hydrocarbonated source, separating into fractions, sending into chlorination reaction chamber and oxychlorination reaction chamber and separating from chambers, Publication date: Jun. 30, 2006, Inventor: Strebelle et al., esp@cenet database—worldwide.

Abstract of FR2883870, Formation of 1, 2-dichloroethane useful in manufacture of vinyl chloride involves subjecting mixture of cracking products obtained by cracking of hydrocarbon source, to a succession of aqueous quenching, alkaline washing, and oxidation steps, Publication date: Oct. 6, 2006, Inventor: Balthasart et al., esp@cenet database—worldwide.

Abstract of FR2883871, Preparing 1, 2-dichloroethane comprises cracking hydrocarbon to form mixture, sending mixture into storage reservoir, supplying mixture into chlorination and/or oxychloration reactor, and separating 1, 2-dichloroethane from reactor, Publication date: Oct. 6, 2006, Inventor: Balthasart et al., esp@cenet database—worldwide.

Abstract of IT1255246, Process for the preparation of dinitrodiphenylmethanes, Publication date: Oct. 20, 1995, Applicant: Enichem Spa et al., esp@cenet database—worldwide.

Abstract of IT1255358, Process for the synthesis of 1, 4-butanediol, Publication date: Oct. 31, 1995, Inventor: Marco, esp@cenet database—worldwide.

Abstract of JP2142740, Production of fluoroalcohol, Publication date: May 31, 1990, Inventor: Tsutomu et al., esp@cenet database—worldwide.

Abstract of JP2144150, Chemical process and catalyst used therefore, Publication date: Jun. 1, 1990, Inventor: Deidamusu et al., esp@cenet database—worldwide.

Abstract of JP4305542, Production of halogenated hydrocarbon compounds, Publication date: Oct. 28, 1992, Inventor: Shinsuke et al., esp@cenet database—worldwide.

Abstract of JP6172225, Method for fluorinating halogenated hydrocarbon, Publication date: Jun. 21, 1994, Inventor: Takashi et al., esp@cenet database—worldwide.

Abstract of JP6206834, Production of tetrachloroethanes, Publication date: Jul. 26, 1994, Inventor: Toshiro et al., esp@cenet database—worldwide.

Abstract of JP8266888, Method for decomposing aromatic halogen compound, Publication date: Oct. 15, 1996, Inventor: Yuuji et al., esp@cenet database—worldwide.

Abstract of JP2001031605, Production of 3-hydroxy-1-cycloalkene, Publication date: Feb. 6, 2001, Inventor: Hideo et al, esp@cenet database—worldwide.

Abstract of JP2004075683, Method for producing optically active halogenohydroxypropyl compound and glycidyl compound, Publication date: Mar. 11, 2004, Inventor: Keisuke et al., esp@cenet database—worldwide.

Abstract of JP2004189655, Method for fluorinating with microwave, Publication date: Jul. 8, 2004, Inventor: Masaharu et al., esp@cenet database—worldwide.

Abstract of JP2005075798, Method for Producing adamantyl ester compound, Publication date: Mar. 24, 2005, Inventor: Norihiro et al., esp@cenet database—worldwide.

Abstract of JP2005082563, Method for producing 1, 3-adamantanediol, Publication date: Mar. 31, 2005, Inventor: Norihiro et al., esp@cenet database—worldwide.

Abstract of JP2005145977, Process for catalytically oxidizing olefin and cycloolefin for the purpose of forming enol, olefin ketone, and epoxide, Publication date: Jun. 9, 2005, Inventor: Cancheng et al., esp@cenet database—worldwide.

Abstract of JP2005254092, Method of manufacturing alkynes, Publication date: Sep. 22, 2005, Inventor: Shirakawa Eiji, esp@cenet database—worldwide.

Abstract of JP2006151892, Preparation method of alcohol derivative, Publication date: Jun. 15, 2006, Inventor: Baba Akio et al., esp@cenet database—worldwide.

Abstract of JP2006152263, Organic-inorganic hybrid-type mesoporous material, method for producing the same, and solid catalyst, Publication date: Jun. 15, 2006, Inventor: Junko et al., esp@cenet database—worldwide.

Abstract of JP2006193473, Aryl polyadamantane derivative having carboxy or acid anhydride group and method for producing the same, Publication date: Jul. 27, 2006, Inventor: Yasuto et al., esp@cenet database—worldwide.

Abstract of JP2006231318, Phosphorus containing macromolecule immobilizing palladium catalyst and method for using the same, Publication date: Sep. 7, 2006, Inventor: Osamu et al., esp@cenet database—worldwide.

Abstract of JP2006263567, Optical resolution method of optical isomer and optical resolution device, Publication date: Oct. 5, 2006, Inventor: Yoshikazu et al., esp@cenet database—worldwide.

Abstract of JP2006265157, Method for catalytically activating silicated nucleating agent using.phosphazene base, Publication date: Oct. 5, 2006, Inventor: Yoshinori et al., esp@cenet database—worldwide.

Abstract of JP2006306758, Method for producing biaryl compound, Publication date: Nov. 9, 2006, Inventor: Yuji et al., esp@cenet database—worldwide.

Abstract of JP2007001942, Production method of para-xylene, Publication date: Jan. 11, 2007, Inventor: Kazuyoshi, esp@cenet database—worldwide.

Abstract of JP2007015994, Method for synthesizing organic compound in ultra high rate under high temperature and high pressure water, and system of high temperature and high pressure reaction, Publication date: Jan. 25, 2007, Inventor: Hajime et al., esp@cenet database—worldwide.

U.S. Office Action from U.S. Appl. No. 10/826,885 dated Oct. 31, 2005.

U.S. Office Action from U.S. Appl. No. 10/826,885 dated Apr. 19, 2006.

U.S. Office Action from U.S. Appl. No. 10/826,885 dated Jul. 27, 2006.

U.S. Office Action from U.S. Appl. No. 10/826,885 dated Nov. 2, 2006.

U.S. Office Action from U.S. Appl. No. 10/826,885 dated Jan. 24, 2007.

U.S. Office Action from U.S. Appl. No. 11/101,886 dated Jan. 24, 2007.

U.S. Office Action from U.S. Appl. No. 11/254,438 dated Jan. 24, 2007.

U.S. Office Action from U.S. Appl. No. 11/254,438 dated Nov. 1, 2007.

U.S. Office Action from U.S. Appl. No. 10/893,418 dated Jan. 2, 2008.

U.S. Office Action from U.S. Appl. No. 10/893,418 dated Jun. 14, 2007.

U.S. Office Action from U.S. Appl. No. 11/091,130 dated Oct. 3, 2007.

U.S. Office Action from U.S. Appl. No. 10/365,346 dated Jun. 12, 2006.

U.S. Office Action from U.S. Appl. No. 11/103,326 dated Aug. 31, 2007.

U.S. Office Action from U.S. Appl. No. 11/103,326 dated Dec. 6, 2006.

U.S. Office Action from U.S. Appl. No. 11/098,997 dated Nov. 20, 2008.

U.S. Office Action from U.S. Appl. No. 12/215,326 dated Feb. 10, 2009.

U.S. Office Action from U.S. Appl. No. 10/430,240 dated Mar. 6, 2006.

U.S. Office Action from U.S. Appl. No. 10/369,148 dated Oct. 16, 2006.

U.S. Office Action from U.S. Appl. No. 10/369,148 dated Mar. 14, 2006.

U.S. Office Action from U.S. Appl. No. 10/894,165 dated Aug. 16, 2006.

U.S. Office Action from U.S. Appl. No. 12/080,594 dated Dec. 22, 2008.

U.S. Office Action from U.S. Appl. No. 11/703,358 dated Jun. 11, 2008.

International Search Report for PCT/US06/010854 dated Jul. 25, 2006.

International Search Report for PCT/US04/023036 dated Jan. 19, 2005.

Office Action from U.S. Appl. No. 12/080,594 dated Jul. 7, 2009.

Office Action from U.S. Appl. No. 12/217,311 dated Feb. 1, 2010.

Office Action from U.S. Appl. No. 12/217,311 dated Jun. 10, 2009.

US 7,964,764 B2

HYDROCARBON SYNTHESIS

CROSS-REFERENCE TO RELATED APPLICATION(S)

This application is a continuation of U.S. patent application Ser. No. 12/080,594 filed Apr. 3, 2008 now abandoned, which is a continuation of Ser. No. 11/091,130, filed Mar. 28, 2005 now abandoned, which is a continuation-in-part of U.S. patent application Ser. No. 10/893,418, filed Jul. 15, 2004 now abandoned, which claims the benefit of U.S. Provisional Patent Application No. 60/487,364, filed Jul. 15, 2003.

FIELD OF THE INVENTION

This invention relates generally to hydrocarbon oligomerization, and more particularly to a method of making hydrocarbons using caloreactants.

BACKGROUND OF THE INVENTION

Scientists have long sought efficient ways to convert methane and other alkanes into higher hydrocarbons, including light olefins and gasoline-range materials. Efficient processes could create value in a number of ways, including: facilitating the utilization of remotely located stranded natural gas through its conversion into more easily transportable liquid fuels and feedstocks, and allowing the use of inexpensive feedstocks (methane and other lower alkanes) for end products often made from higher alkanes, including ethylene and propylene.

U.S. Pat. Nos. 6,486,368, 6,472,572, 6,465,699, 6,465, 696, and 6,462,243 disclose processes for converting alkanes into olefins, ethers, and alcohols. Many of the disclosed processes involve halogenation of an alkane, passing the halogenated products over a metal oxide to create products and metal halide, recovering the product(s), and regenerating the metal halide with oxygen or air to yield metal oxide and halogen for recycle to the process. Not described is alkane oligomerization: substantial coupling of the starting hydrocarbon to obtain product(s) of higher carbon number.

Several investigators have examined the use of halogenation for the production of higher hydrocarbons from methane. Representative patents include U.S. Pat. No. 4,513,092 (Chu), U.S. Pat. No. 4,769,504 (Noceti and Taylor), U.S. Pat. No. 5,087,786 (Nubel), and U.S. Pat. No. 6,452,058 (Schweitzer). As described in the Taylor patent: "Aromatic-rich, gasoline boiling range hydrocarbons [are made] from the lower alkanes, particularly from methane. The process is carried out in two stages. In the first, alkane is reacted with oxygen and hydrogen chloride over an oxyhydrochlorination catalyst such as copper chloride with minor proportions of potassium chloride and rare earth chloride. This produces an intermediate gaseous mixture containing water and chlorinated alkanes. The chlorinated alkanes are contacted with a crystalline aluminosilicate catalyst in the hydrogen or metal-promoted form to produce gasoline range hydrocarbons with a high proportion of aromatics and a small percentage of light hydrocarbons ($C_2$-$C_4$), as well as reforming the HCl. The light hydrocarbons can be recycled for further processing over the oxyhydrochlorination catalyst." All of these techniques for making higher alkanes from $C_1$ feedstocks suffer from the disadvantage that the hydrocarbon stream must be separated from an aqueous hydrohalic acid stream, and the hydrohalic acid stream must be recycled.

U.S. Pat. No. 4,795,843 (Tomotsu et al.) discloses a process for oligomerizing halomethanes to products including ethyl benzene, toluene, and xylenes, using silica polymorph or silicalite catalysts. The process does not incorporate reactive neutralization of hydrogen halide, and appears to suffer from slow kinetics.

In a process for halogenating hydrocarbons, Chang and Perkins noted trace amounts of oligomerization products in the presence of zeolites in U.S. Pat. No. 4,654,449. The oligomerization products were low in quantity, and generally halogenated.

U.S. Pat. No. 4,373,109 (Olah) discloses a process for converting heterosubstituted methanes, including methyl halides, by contacting such methanes with bifunctional acid-base catalysts at elevated temperatures, between 200 and 450 C, preferably between 250 and 375 C, to produce predominantly lower olefins, preferably ethylene and propylene. The catalysts of preference are those derived from halides, oxyhalides, oxides, sulfides or oxysulfides of transition metals of Groups IV, V, VI, VIII of the Periodic Table, such as tantalum, niobium, zirconium, tungsten, titanium, and chromium, deposited on acidic oxides and sulfides such as alumina, silica, zirconia or silica-alumina. Neither the use of solid oxide-based halogen recovery nor the formation of alcohols or ethers is disclosed. A related reference is "Ylide chemistry. 1. Bifunctional acid-base-catalyzed conversion of heterosubstituted methanes into ethylene and derived hydrocarbons. The oniuin-ylide mechanism of the C1→C2 conversion" by George A. Olah et al. (J. Am. Chem. Soc. 106, 2143 (1984)).

U.S. Pat. No. 3,894,107 (Butter, et al.) discloses improvements to a process for condensing halogenated hydrocarbons using zeolite catalysts. Notably absent is any discussion of solid oxide-based hydrogen halide neutralization.

Kochi has observed reductive coupling of alkyl halides when transition metal bromides are reacted with low-molecular weight Grignard reagents in THF or diethyl ether (Bulletin of the Chemical Society of Japan v. 44 1971 pp. 3063-73). Liquid phase chemistry, however, typically suffers from such disadvantages as the requirement of solvent, corrosion, and lower rates of reaction than gas-phase chemistry. In addition, such a process consumes energy required to produce the magnesium metal needed for the energetic and reducing Grignard reagents. This is not the same type of process as the dehydrohalogenative coupling and hydrogen halide neutralization we describe herein.

SUMMARY OF THE INVENTION

The present invention addresses the need for an efficient way to convert methane and other hydrocarbons into higher hydrocarbons. In one embodiment, a hydrocarbon having a carbon number $C_n$, where $n \geq 2$, is prepared by allowing a reactant hydrocarbon having a carbon number $C_m$, where $m < n$, to react with a halogenating agent, thereby forming a halogenated hydrocarbon; allowing the halogenated hydrocarbon to contact a metal-oxygen cataloreactant, thereby forming a product hydrocarbon having an carbon number $C_n$, where $n \geq 2$; recovering the product hydrocarbon; and regenerating the cataloreactant. Often, a mixture of hydrocarbons is obtained, but careful selection of the reactant hydrocarbon, halogenating agent, metal-oxygen cataloreactant, and reaction conditions allow a tailored approach to hydrocarbon product formation. Methane (i.e., natural gas) as well as other light hydrocarbons, e.g., $C_2$ to $C_6$ hydrocarbons, are envisioned as preferred feedstocks. More generally, the invention contemplates the use of feedstocks having carbon numbers as high as $C_{10}$. Laboratory observations have thus far focused on methane oligomerization and methyl bromide coupling, with detection of $C_2$-$C_{10}$ species, including alkanes, alkenes, branched hydrocarbons, and aromatic compounds.

DETAILED DESCRIPTION OF THE INVENTION

The present invention exploits the discovery that metal-oxygen compounds, such as mixed metal oxides, doped zeolites (i.e., alkaline-earth metal-doped zeolites), metal oxide-impregnated zeolites, etc., facilitate hydrocarbon oligomerization. According to one aspect of the invention, a hydrocarbon having a carbon number $C_n$, where $n \geq 2$, is formed by (i) forming a halogenated hydrocarbon by allowing a reactant hydrocarbon having a carbon number $C_m$, where $m < n$, to react with a halogenating agent; (ii) forming a product hydrocarbon having a carbon number $C_n$, where $n \geq 2$, by allowing the halogenated 5 hydrocarbon to contact a metal-oxygen cataloreactant; (iii) recovering the product hydrocarbon; and (iv) regenerating the cataloreactant.

More generally, the method entails the steps of halogenation, oligomerization, product recovery, and cataloreactant regeneration. The halogenated products may be separated from the unreacted (non-halogenated) hydrocarbon either before or after reaction with the metal-oxygen cataloreactant. Neutralization of any hydrohalic acid formed during the synthesis is advantageously accomplished concomitantly with carbon-carbon coupling and/or cataloreactant regeneration. Preferably, the process is an integrated one and takes place, for example, in a zone reactor, as described, for example, in U.S. Pat. No. 6,525,230 (Grosso), the entire contents of which is incorporated by reference herein. Thus, halogenation of methane or other hydrocarbons occurs within one zone of the reactor, and is followed by a condensation step in which the liberated hydrohalic acid is adsorbed within the same bifunctional material that catalyzes condensation of the halogenated hydrocarbon. Hydrocarbon oligomerization (defined as carbon-carbon coupling) takes place within this zone of the reactor and yields product hydrocarbons which, in general, will have carbon numbers ranging from $C_2$ to $C_{20}$, and may include alkanes, alkenes, alkynes, and/or aromatics. Treatment with air or oxygen liberates halogen for use in subsequent halogenation steps, and regenerates the cataloreactant material for subsequent condensation or metathesis. Advantageously, the need for recycling/recovering corrosive, aqueous hydrohalic acid is avoided because regeneration and recovery takes place in situ.

Higher hydrocarbon synthesis begins with a hydrocarbon feedstock: one or more reactant hydrocarbons, each having, independently, a carbon number $C_m$, where $m < n$, $C_n$ being the carbon number of the target hydrocarbon(s). Non-limiting examples of reactant hydrocarbons include methane, ethane, propane, etc., with natural gas (predominately methane, but often including small amounts of $C_2$ and higher species) being preferred. In general, the starting hydrocarbon has a carbon number between 1 and 10. Mixtures of hydrocarbons may also be used.

The reactant hydrocarbons are allowed to react with a halogenating agent. Non-limiting examples include molecular halogen (e.g., bromine, chlorine, etc.), alkyl halides (e.g., dibromomethane, bromoform, carbon tetrabromide), and condensed halides, such as metal bromides, which may be present as a solid, liquid, supported, or unsupported material.

Molecular halogens are preferred, with bromine ($Br_2$) being most preferred. Bromine is a liquid at room temperature, less reactive than chlorine and fluorine, and easy to handle. Bromine also has favorable energetics.

The reduction potential of bromine to bromide is 1.07 V vs. NHE, while that of oxygen to water is 1.23 V. A broad range of metal bromides may release bromine upon treatment with oxygen. At the same time, alkane bromination and subsequent alkyl bromide coupling and HBr neutralization are only mildly exothermic, but spontaneous enough to go to completion. Water and coupled hydrocarbons are the only fluid products. The same is not true with chlorine as mediator, for which HCl is a major component of the product stream. Hydrogen chloride production requires separation, drying, and recycling, which is costly. In short, the thermochemistry of metal bromide-mediated alkane partial oxidation is well-suited for efficient and inexpensive plant operation.

Halogenation of the reactant hydrocarbon may proceed in a number of ways, depending in part on the desired product(s) and in part on the feed. In one embodiment, an alkane is halogenated with molecular halogen using heat, light, or other electromagnetic radiation to drive the reaction, with heat being preferred. There is some benefit in having all steps—halogenation, oligomerization, and regeneration (described below)—occur at roughly the same temperature. For methanol to olefin (MTO) and methanol to gasoline (MTG) processes, temperatures of from 375 to 450° C. are utilized, with the range being important, if not critical. For the carbon-carbon coupling process described herein, an ideal temperature range, where all steps occur at roughly the same temperature, is 450 to 550° C.

However, individual reaction steps might be carried out at temperatures above or below this range. Indeed, gasoline yields are better at lower reaction temperatures and, in some of the examples below, the reaction of methyl bromide with an alkaline-earth metal-doped zeolite is carried out at a temperature of from 225 to 350° C. and a pressure of from 1 to 5 bar (14.5 to 72.5 psi). For a fully integrated process, however, the engineering favors running all three reactions at a similar temperature.

Halogenation preferably occurs at a pressure between 0.1 and 200 atm for the subsequent carbon-carbon step. Low pressure favors less carbon-carbon coupling (i.e., a smaller average molecular weight of product), while high pressure favors higher coupling. Processes for light olefins are likely to run at the same 60 to 200 psia that methanol to olefin (MTO) processes are run at, although higher pressures may alternatively be utilized. For production of gasoline-range molecules, pressures around 350 psia, as used in methanol to gasoline (MTG) processes, are envisioned. As a practical matter, running below atmospheric (more conservatively, below 2 psia) or above 100 atm is unlikely.

When molecular halogen is used as the halogenating agent, halogenation ideally is carried out at an alkane:halogen ratio of between 1:10 and about 100:1, on a volume by volume basis. At alkane:halogen ratios of less than 1:10 (i.e., more halogen), multi-halogenated hydrocarbons will be formed, typically leading to complete oxidation (i.e., $CO_2$) upon subsequent contact with the metal-oxygen cataloreactant. At alkane:halogen ratios higher than 100:1, the conversion to a halogenated hydrocarbon will be too low, perhaps 1% or less, and it is nearly impossible to imagine an economical process at such conversion levels. (30-60% conversion are more likely lower limits).

Altering the, ratio of halogen to alkane or other hydrocarbon feedstock may have a marked impact on product distribution. For example, one may choose to control the degree of halogenation in order to reduce aromatic formation in the production of lower olefins or fuels. A second example is minimizing formation of highly halogenated methane in order to reduce the formation of alkynes.

A key feature of the invention is the use of a metal-oxygen cataloreactant, which facilitates carbon-carbon coupling, i.e., hydrocarbon oligomerization. The term "metal-oxygen cataloreactant" is used herein to refer to a cataloreactant material containing both metal and oxygen. While not bound by theory, it is believed that the material catalyzes carbon-carbon coupling via hydrogen halide (e.g., HBr) elimination and alkylidene insertion into cationically activated C—H and possibly C—C bonds. The cataloreactant also acts as a halogen release and sequestering agent, and offers the possibility of obtaining a tunable coupling product distribution, including the ability to produce oxygenates if desired, while simultaneously trapping and recovering halogen, emitting only water as a byproduct. Treatment with air or oxygen regenerates the cataloreactant.

Nonlimiting examples of metal-oxygen cataloreactants include zeolites, doped zeolites, metal oxides, mixed metal oxides, metal oxide-impregnated zeolites, and similar materials, as well as mixtures of such materials. Nonlimiting examples of dopants include alkaline-earth metals, such as calcium and magnesium, and their oxides and/or hydroxides.

Zeolites are available from a variety of sources, including Zeolyst International (Valley Forge, Pa.). Specific examples include doped-ZSM-5 and doped mordenite (where, e.g., calcium and/or magnesium are the dopants).

Shifting the properties of the zeolite or zeolite component of a zeolite/metal oxide composite is also expected to shift product distribution. Pore size and acidity are particularly expected to be important. Acidity may be used to control chain length and functionality, and pore size may control chain length and functionality. Zeolites of particular pore-size may, selectively produce benzene, toluene, para-xylene, ortho-xylene, meta-xylene, mixed xylenes, ethyl benzene, styrene, linear alkyl benzene, or other aromatic products. The use of pore size is not limited to aromatic products.

In one embodiment of the invention, a metal oxide/zeolite composite is prepared by mixing a zeolite with a metal nitrate (e.g., an alkaline-earth metal oxide, such as calcium nitrate) or hydrated species thereof, and then calcining this mixture to release nitrogen oxides and retain the metal oxide-impregnated zeolite.

After oligomerization, the metal-oxygen cataloreactant is regenerated by treatment with air or oxygen, typically at a temperature of from 200 to 900° C. This converts metal halide species into metal-oxygen species.

A number of variables, including feed composition, feed location in the reactor, temperature, pressure, metal oxide composition, and reactor residence time may alter the product distribution. Production of alkanes, olefins and aromatics from methane has been detected and confirmed. Also expected is the ability to produce alkanes and olefins of particular branching (including mono-methyl branched alcohols), alcohols, diols, ethers, halogenated hydrocarbons, aromatics including benzene, styrene, ethyl benzene, toluene, xylenes, and linear alkyl benzenes, and hydrocarbons suitable for fuels such as gasoline, diesel, and jet fuel.

Control of the feed composition can control the product distribution. First, hydrogen halide produced in the halogenation may be neutralized (to form water or alcohol) with the same metal-oxygen compound producing the hydrocarbon product(s), or with a separate metal-oxygen compound in a distinct reactor. Shifting the hydrogen halide neutralization location may shift the product distribution, including functionality, chain length, and branching. For example, concurrent neutralization and product formation may be expected to drive the production of alcohols, which may or may not undergo further reactions such as coupling or dehydration. Second, water addition to the feed may shift product distribution. In particular, the addition of water may favor alcohol products. The addition of water may also control degree and type of branching and chain length. Third, hydrogen addition may alter the product distribution. Hydrogen may increase alkanes at the expense of other functionalities, something particularly useful for producing fuels. Hydrogen may also reduce coking and help control the chain length and branching.

It will also be appreciated that carbon-carbon oligomerization may proceed by a number of pathways. Even single-hydrocarbon feedstocks may yield more than one product. On the other hand, in one embodiment of the invention, controlled halogenation is used to produce predominately one isomer in favor of another (e.g., selective formation of 1-butene or 2-butene). Mixed feedstocks, such as raw natural gas, may give rise to oligomerization of multiple halogenated hydrocarbons (e.g., ethyl halide, dihaloethane, methyl halide, methyl dihalide, propyl halide, propyl dihalide, etc.). Indeed, in one embodiment of the invention, an alkyl halide is purposefully introduced to create desired branched products. An example would be oligomerization of methyl halide (from methane) with ethyl halide or a higher alkyl halide to produce, selectively, methyl, ethyl, propyl, isopropyl, or tertiary butyl (or other) branching. Another example might be the synthesis of styrene from ethyl halide, methyl halide, and dihalomethane.

In one embodiment of the invention, the reaction of halogenated hydrocarbon with a metal-oxygen cataloreactant takes place in a fluidized bed. Alternatively, a fixed bed is employed. Different alkyl halides may be introduced at different locations in the reactor. One example is the introduction of methyl halides at one location in a reactor to produce benzene, to which ethyl halides are added, producing styrene or ethyl benzene. Another example is the introduction of methyl halides at one location in a reactor to produce benzene, to which alkyl halides are added, producing linear alkyl benzene.

Product separation is accomplished by any suitable method. Nonlimiting examples include distillation, adsorption, and extraction. Product(s) may be recovered from the solid by stripping with steam, carbon dioxide, or other means.

The following are nonlimiting examples of the invention:

EXAMPLE 1

Metal Oxide/Zeolite composite MZ1 was prepared as follows: A solid mixture of a ZSM-5-type zeolite (Zeolyst CBV 8014, Si/Al ratio=80:1, 10 g, 170 mmoles $SiO_2$) and $CaNO_3$ nonahydrate (9 g, =34 mmoles Ca) was prepared and water was added to incipient wetness. After $CaNO_3$ dissolution and stirring, the slurry was dried and calcined in sequence at 115° C. (overnight) and 500° C. (overnight), respectively, in air.

EXAMPLE 2

Methane at 15 psia was bubbled through bromine at 1° C. at a rate of 5 cc/min. The resulting stream of bromine and methane (1:10 by mole) was passed through a small diameter bromination reactor at 450° C. (1000 $h^{-1}$) and the mixture of $CH_{4-x}Br_x$ (x=0, 1, 2, 3) passed into a reactor containing 5 g of metal oxide/zeolite composite MZ1 (400 C). The output stream from the second reactor contained no brominated products. Based on the methane consumed in the bromination reactor, 10% ethylene, 31% propylene, 3% propane, and 21% butanes/butenes were detected; 65% overall. Trace amounts of $C_6$ species were also detected. After reaction for 5 hours, during which the stream output did not change from the distribution described above, the methane stream was discontinued and the reactor was purged with helium at 5 cc/min for 10 minutes. After He purge, a flow of $O_2$ (2 cc/min) into the second reactor was initiated at 525 C to regenerate the metal oxide from the metal bromide of the partially spent composite. Initially only water and $CO_2$ were observed as products, but abruptly the stream contents changed to $Br_2$ and unreacted $O_2$. After 1 hour, the $O_2$ purge was discontinued and the reactor was again purged with helium. The caustic trap used during regeneration was tested for $CO_3^{-2}$ and 1.0 mmol was found, representing 24% of the converted carbon. The remainder of carbon was found to be higher boiling volatile aromatics (mostly toluene, xylenes and mesitylenes). A second cycle of bromomethanes condensation as described above was initiated at 400° C. and the product distribution was found to be identical to the first run. Three more cycles of condensation/neutralization/regeneration produced the same output of higher hydrocarbons.

EXAMPLE 3

A doped mordenite (Zeolyst CBV 21A, doped with both Ca and Mg) (5 g) was prepared according to Example 1, and used as the cataloreactant in a hydrocarbon synthesis substantially similar to that described above in Example 2. The product output was 30% ethylene, 5% ethane, 10% propylene, 3% propane, 5% butanes/butenes. Multiple runs and cataloreactant regeneration established reproducibility.

EXAMPLES 4-15

A ZSM-5-type zeolite (Zeolyst CBV 28014, having a 280:1 Si:Al ratio) from Zeolyst Corp. was doped with calcium according to the procedure described in Example 1, to a 4:1 Ca:Si ratio. A glass reaction tube (6 in. length; 4 mm inner diameter) was charged with 1.427 g of the coarsely ground, calcium-doped zeolite, and a stream of methyl bromide (4.5 mmol) was caused to flow into the tube. After conversion of methyl bromide, the solid was regenerated by treatment with $O_2$ (2 sccm, 1 bar) at 520 C for 3 hours, and evolved $Br_2$ was recovered. The methyl bromide coupling reaction was performed over a range of pressures, temperatures, and flow rates using the same solid and same amount of methyl bromide per run. Products and any unreacted methyl bromide exited the opposite end of the reaction tube and were analyzed by one or more of GC, GC/MS, and NMR. Due to unmistakable isotope ratios and fragmentation patterns, GC/MS is particularly useful as a diagnostic of bromohydrocarbon content (which, typically, is zero).

Table 1 summarizes the hydrocarbon product distributions (also referred to as "selectivity" (sel), expressed as a percentage), percent conversion of $CH_3Br$, and reaction parameters, T, P, and τ (space time), where τ was calculated according to the equation: τ=reactor volume/incoming flow rate. Aromatic product distributions are underscored.

TABLE 1

Examples 4-15: $CH_3Br$ coupling over Ca-doped ZSM-5:
Reaction parameters and products

| Ex. | Conv. % | T, °C. | P, bar | τ, sec | C11 | C2 | C3 | C4 | C5 | C6 | C7 | C8 | C9 | C10 |
|---|---|---|---|---|---|---|---|---|---|---|---|---|---|---|
| 4 | 65 | 225 | 5 | 60 | 0.4 | 0.2 | 5.8 | 21.8 | 18.8 | 14.5 | 11.7 | 12.8 | 5.8 | 4.2 |
| 5 | 90 | 250 | 5 | 6 | 0.5 | 0.4 | 6.1 | 30.2 | 22.5 | 18.3 | 12.3 | 7.6 | 2.1 | |
| 6 | 95 | 250 | 5 | 20 | 0.3 | 0.3 | 6.9 | 22.4 | 20.2 | 16.3 | 13.5 | 12.7 | 5.6 | 2.1 |
| 7 | 97 | 250 | 5 | 60 | 0.4 | 0.3 | 5.6 | 19.9 | 18.5 | 15.2 | 13.2 | 13.0 | 8.4 | 5.6 |
| 8 | 97 | 250 | 1 | 12 | 0.2 | 0.2 | 6.1 | 21.4 | 21.5 | 18.5 | 14.0 | 9.7 | 6.0 | 2.2 |
| 9 | 95 | 275 | 5 | 6 | 0.4 | 0.7 | 9.9 | 27 | 20.7 | 18.2 | 13.5 | 7.6 | 2.1 | |
| 10 | 100 | 275 | 3 | 50 | 1.8 | 2 | 4.4 | 16.2 | 18.2 | 16.1 | 13.8 | 12.5 | 6.3 | 2.5 |
| | | | | | | | | | | | _0.9_ | _1.6_ | _2.5_ | _1.2_ |
| 11 | 97 | 300 | 5 | 6 | 0.5 | 0.8 | 11.4 | 26.5 | 19.6 | 17 | 13.3 | 8.2 | 2.6 | |
| 12 | 100 | 350 | 3 | 8 | 1.0 | 1.5 | 14.6 | 26.7 | 19.4 | 15.2 | 10.1 | 6.2 | 2.8 | 0.8 |
| | | | | | | | | | | | _0.6_ | _1.3_ | _0.9_ | _0_ |
| 13 | 100 | 350 | 3 | 16 | 1.0 | 2.0 | 11.9 | 25.2 | 19.1 | 13.8 | 9.4 | 6.9 | 2.6 | 0.0 |
| | | | | | | | | | | | _1.6_ | _4.5_ | _2.1_ | _0.9_ |
| 14 | 100 | 350 | 3 | 50 | 1.1 | 2.2 | 15.5 | 25.4 | 14.6 | 9.1 | 5.4 | 3.2 | 0.8 | 0.0 |
| | | | | | | | | | | | _4.6_ | _10.8_ | _4.9_ | _3.4_ |
| 15 | 100 | 350 | 3 | 100 | 1.2 | 1.9 | 16.7 | 19.8 | 10.5 | 7.8 | 3.6 | 2.3 | 0.9 | 0.0 |
| | | | | | | | | | | | _8.4_ | _17.7_ | _9.2_ | _1.1_ |

As seen in Table 1, an alkaline-earth metal-doped zeolite facilitated the conversion of a brominated alkane ($CH_3Br$) into a number of different hydrocarbons, including linear and branched alkanes, olefins, and aromatic compounds. Water was also produced, as a byproduct of HBr neutralization. GC analysis of products showed high conversions of methyl bromide (with lower conversions occurring at low temperatures, and higher conversions occurring at high temperatures), and pH measurements showed complete neutralization of HBr formed in the reaction.

In general, the percentage of $C_5$ and higher hydrocarbons produced for a given run exceeded 70%, and the percentage of $C_6$ and higher hydrocarbons produced exceeded 50%. Detected aromatic compounds include toluene ($C_7$), xylenes and ethylbenzene ($C_8$), mesitylenes and ethylmethylbenzene ($C_9$), and higher hydrocarbons (e.g., $C_{10}$). In some runs, a small amount of benzene was detected.

Although not bound by theory, the carbon-carbon coupling appears to proceed in two stages, similar to what is observed with the formations of hydrocarbons from methanol coupling. In a first, rapid stage, olefins appear to form, couple, and then crack. This appears to be followed by a slower, second stage yielding aromatic products and paraffins after longer exposure to the catalyst and higher temperatures.

It has been observed that freshly prepared solid cataloreactant does not give the "steady state" product distribution obtained after 1 cycle (an repeated for a number of additional cycles) of coupling/bromine sequestering, followed by solid reoxygenation and bromine release. That is, "first run" product distributions are dissimilar from the distributions seen using recycled solid cataloreactant.

EXAMPLES 16-18

To demonstrate that lighter hydrocarbons can be recycled into the coupling reactor, first propylene (4.5 mmol), and then a mixture of $CH_3Br$ and propylene (3:1 v/v or 3.3 mmol:1.1 mmol) were utilized as a feed in a glass reaction tube configured as described in Examples 4-15. The product distribution was compared to that obtained using $CH_3Br$ (4.5 mmol) alone. The results are presented in Table 2. Aromatic product distributions are underscored.

TABLE 2

Examples 16-18: Reaction products for propylene (Ex. 16); 3:1 $CH_3Br$: propylene (Ex. 17); and $CH_3Br$ alone (Ex. 18) over Ca-doped ZSM-5.

| Ex. | Conv. % | T, °C. | P, bar | τ, sec | $C_1$, sel | $C_2$ | $C_3$ | $C_4$ | $C_5$ | $C_6$ | $C_7$ | $C_8$ | $C_9$ | $C_{10}$ |
|---|---|---|---|---|---|---|---|---|---|---|---|---|---|---|
| 16 | n.a. | 325 | 3 | 16 | 0.1 | 0.6 | 9.7 | 16.3 | 21.0 | 18.1 | 13.8 | 9.9 | 6.3 | 2.5 |
|    |      |     |   |    |     |     |     |      |      |      | 0.4  | 0.5 | 0.6 | 0.4 |
| 17 | 100  | 300 | 3 | 16 | 0.2 | 0.5 | 8.3 | 18.4 | 19.0 | 16.7 | 14.2 | 10.9 | 7.0 | 3.2 |
|    |      |     |   |    |     |     |     |      |      |      | 0.3  | 0.5 | 0.4 | 0.3 |
| 18 | 95   | 300 | 3 | 16 | 0.5 | 0.6 | 8.6 | 23.7 | 19.3 | 16.2 | 12.8 | 9.3 | 5.7 | 1.9 |

Table 2 shows that the less desirable (from the standpoint of gasoline production) light olefins may be recycled into the feed stream for incorporation into heavier products. The fact that the product distribution for a propylene feed is similar to that for MeBr and MeBr/propylene 1:1 (C:C basis) shows that recycling of light olefins will improve the overall yield of gasoline products.

The invention has been described by reference to various examples and preferred embodiments, but is not limited thereto. Other modifications and substitutions can be made without departing from the scope of the invention. For example, the oligomerization processes described herein are also intended to encompass halogenation of olefin feedstocks using a hydrogen halide (e.g., HBr) or molecular halogen; halogenation of acetylenes (alkynes) using hydrogen halide or molecular halogen; halogenation of alcohols or ethers using hydrogen halide or molecular halogen; and halogenation of alkanes using molecular halogen and a catalyst that controls the halogenation. Specifically, the catalyst may control one or both of the degree of halogenation (number of halogens per molecule) and the position of halogenation (e.g. terminal vs. internal halogenation for a long chain alkane). Other modifications may be made as well. The invention is limited only by the appended claims and equivalents thereof.

What is claimed is:

1. A method of making a product hydrocarbon having a carbon number $C_n$, where n>2, comprising:
   reacting a halogenating agent with a reactant hydrocarbon having a carbon number $C_m$, where m<n, to form a halogenated hydrocarbon;
   contacting the halogenated hydrocarbon with a first solid metal-oxygen cataloreactant to form a hydrogen halide and a plurality of product hydrocarbons having a carbon number $C_n$, where n>2;
   contacting the hydrogen halide with a second solid metal-oxygen cataloreactant to form a halogenated cataloreactant;
   recovering the product hydrocarbons; and
   contacting the halogenated cataloreactant with oxygen or air to regenerate the cataloreactant and form a molecular halogen.

2. The method of claim 1 further comprising:
   recycling the molecular halogen as the halogenating agent to react with the reactant hydrocarbon.

3. The method of claim 1 wherein the first solid cataloreactant and the second solid cataloreactant are the same solid cataloreactant.

4. The method of claim 1 wherein the first solid cataloreactant or the second solid cataloreactant is a zeolite doped with an alkaline-earth metal.

5. The method of claim 4 wherein the zeolite has an Si:Al ratio of from about 80:1 to 280:1.

6. The method of claim 4 wherein the zeolite has an Si:Al ratio of about 80:1.

7. The method of claim 4 wherein the zeolite has an Si:Al ratio of about 280:1.

8. The method of claim 4 wherein the zeolite doped with an alkaline-earth metal has an alkaline earth metal:silicon ratio of about 4:1.

9. The method of claim 1 wherein the product hydrocarbons comprise at least one aromatic hydrocarbon.

10. The method of claim 9 wherein the at least one aromatic hydrocarbon comprises at least one hydrocarbon selected from the group consisting of benzene, toluene, xylene, ethylbenzene, mesitylene, and ethylmethylbenzene.

11. The method of claim 1 wherein the product hydrocarbons comprise at least one branched alkane.

12. The method of claim 1 wherein the product hydrocarbons comprise at least one olefin.

13. The method of claim 1 wherein the product hydrocarbons comprise at least one alkane, at least one olefin, and at least one aromatic hydrocarbon.

14. The method of claim 1 wherein the product hydrocarbons comprise a gasoline grade mixture of hydrocarbons.

15. The method of claim 1 further comprising allowing any $C_1$ to $C_3$ hydrocarbons, which are formed from allowing the halogenated hydrocarbon to contact the first solid metal-oxygen cataloreactant, to contact the first solid metal-oxygen cataloreactant again to form one or more $C_4$ or higher hydrocarbons.

16. The method of claim 15 wherein at least a portion of the $C_1$ to $C_3$ hydrocarbons comprise at least one olefin.

17. The method of claim 1 wherein the halogenating agent comprises bromine.

18. The method of claim 1 wherein the first solid metal-oxygen cataloreactant is contacted with the halogenated hydrocarbon in a fixed bed.

19. The method of claim 1 wherein the second solid metal-oxygen cataloreactant is contacted with the hydrogen halide in a fixed bed.

20. The method of claim 1 wherein the first solid metal-oxygen cataloreactant is contacted with the halogenated hydrocarbon in a fluidized bed.

21. The method of claim 1 wherein the second solid metal-oxygen cataloreactant is contacted with the hydrogen halide in a fluidized bed.

22. A method of making a product hydrocarbon having a carbon number $C_n$, where n>2, comprising:
   reacting a halogenating agent with a reactant hydrocarbon having a carbon number $C_m$, where m<n, to form a halogenated hydrocarbon;

contacting the halogenated hydrocarbon with a first solid metal-oxygen cataloreactant to form a hydrogen halide and a plurality of product hydrocarbons having a carbon number $C_n$, where n>2, at least 50% of which are $C_6$ or higher hydrocarbons;

contacting the hydrogen halide with a second solid metal-oxygen cataloreactant to form a halogenated cataloreactant;

recovering the product hydrocarbons; and contacting the halogenated cataloreactant with oxygen or air to regenerate the cataloreactant and form a molecular halogen.

23. The method of claim 22 wherein the first solid cataloreactant and the second solid cataloreactant are the same solid cataloreactant.

24. A method of making a product hydrocarbon having a carbon number $C_n$, where n>2, comprising:

reacting a halogenating agent with a reactant hydrocarbon having a carbon number $C_m$, where m<n, to form a halogenated hydrocarbon;

contacting the halogenated hydrocarbon with a first solid metal-oxygen cataloreactant to form a hydrogen halide and a plurality of product hydrocarbons having a carbon number $C_n$, where n>2, at least 70% of which are $C_5$ or higher hydrocarbons;

contacting the hydrogen halide with a second solid metal-oxygen cataloreactant to form a halogenated cataloreactant;

recovering the product hydrocarbons; and contacting the halogenated cataloreactant with oxygen or air to regenerate the cataloreactant and form a molecular halogen.

25. The method of claim 24 wherein the first solid cataloreactant and the second solid cataloreactant are the same solid cataloreactant.

26. A method of making a product hydrocarbon having a carbon number $C_n$, where n>2, comprising:

reacting a halogenating agent with a reactant hydrocarbon having a carbon number $C_m$, where m<n, to form a halogenated hydrocarbon;

contacting the halogenated hydrocarbon with a first solid metal-oxygen cataloreactant to form a hydrogen halide and a plurality of product hydrocarbons having a carbon number $C_n$, where n>2, at least 50% of which are $C_6$ or higher hydrocarbons, and at least 70% of which are $C_5$ or higher hydrocarbons;

contacting the hydrogen halide with a second solid metal-oxygen cataloreactant to form a halogenated cataloreactant;

recovering the product hydrocarbons; and contacting the halogenated cataloreactant with oxygen or air to regenerate the cataloreactant and form a molecular halogen.

27. The method of claim 26 wherein the first solid cataloreactant and the second solid cataloreactant are the same solid cataloreactant.

* * * * *